(12) United States Patent
Neelam et al.

(10) Patent No.: US 6,969,588 B2
(45) Date of Patent: Nov. 29, 2005

(54) ISOLATED HUMAN RAS-LIKE PROTEINS, NUCLEIC ACID MOLECULES ENCODING THESE HUMAN RAS-LIKE PROTEINS, AND USES THEREOF

(75) Inventors: Beena Neelam, Gaithersburg, MD (US); Karen A. Ketchum, Germantown, MD (US); Valentina Di Francesco, Rockville, MD (US); Ellen M. Beasley, Damestown, MD (US)

(73) Assignee: Applera Corporation, Norwalk, CT (US)

( * ) Notice: Subject to any disclaimer, the term of this patent is extended or adjusted under 35 U.S.C. 154(b) by 632 days.

(21) Appl. No.: 09/778,963

(22) Filed: Feb. 8, 2001

(65) Prior Publication Data

US 2002/0115172 A1 Aug. 22, 2002

(51) Int. Cl.[7] .......................... C12Q 1/68; C12N 15/00; C12N 15/63; C12N 5/10; C07H 21/04
(52) U.S. Cl. ..................... 435/6; 435/69.1; 435/320.1; 435/325; 435/252.3; 435/254.11; 536/23.5; 536/24.5
(58) Field of Search ........................ 435/6, 69.1, 320.1, 435/325, 252.3, 254.11; 536/23.5, 24.5, 23.1

(56) References Cited

FOREIGN PATENT DOCUMENTS

| WO | WO 99 58670 A | 11/1999 |
|---|---|---|
| WO | WO 02 10217 A | 2/2002 |

OTHER PUBLICATIONS

Verma et al (Nature, 1997, vol. 389, pp. 239–242).*
Eck et al (Gene-Based Therapy, In: The Pharmacological Basis of Therapeutics, Goodman and Gilman, Ed.s, 1996, pp. 77–101).*
Orkin et al state ("Report and Recommendation of the Panel to Assess the NIH investment in Research on Gene Therapy", NIH, 1995).*
Houdebine, Journal of Biotechnology, 1994, vol. 34, pp. 269–287.*
St. Croix B. et al. "Genes Expressed in Human Tumor Endothelium." Science. vol. 289, No. 5482, Aug. 18, 2000, pp. 1197–1202, XP002222041.
Falk Jeffrey D. et al. "Rhes: A Striatal-Specific Ras Homolog Related to Dexrasl." Journal of Neuroscience Research. vol. 57, No. 6, pp. 782–788. XP009001294.
Adachi J. et al. "Mus Musculus Adult Make Testis cDNA, RIKEN Full-Length Enriched Library, Clone: 49305262B11: Homolog to REHS Protein, Full Insert Sequence." Database accession, No. AK015898. XP002222042.
International Search Report dated Dec. 11, 2002.
Results of BLAST search of SEQ ID No. 2 against Derwent (FastAlert and GeneSeqP) and NCBI (pataa) protein patent databases on Jun. 26, 2003.

* cited by examiner

*Primary Examiner*—Karen A. Canella
(74) *Attorney, Agent, or Firm*—Celera Genomics; Justin D. Karjala

(57) ABSTRACT

The present invention provides amino acid sequences of polypeptides that are encoded by genes within the human genome, the Ras-like protein polypeptides of the present invention. The present invention specifically provides isolated polypeptide and nucleic acid molecules, methods of identifying orthologs and paralogs of the Ras-like protein polypeptides, and methods of identifying modulators of the Ras-like protein polypeptides.

10 Claims, 12 Drawing Sheets

```
   1 GGCGTCGCCG CGCGGGGAGA AAGAAGCCGC GCCCAGCCCG GCGTCCCGAG
  51 CAGCGCAGGG GAGGATCCCC GCGCAGTGAC CCGGGAGCCA CCACAGACTC
 101 TGGGAGGCTC GGCGGCTGGA GCAGCAGGCA GCTCCCCGCA GCTCCCGGCG
 151 CTTCCAGGCA GCTCTCTGAG CCGTGCCAGA GGCCCGGCCC GCCATTCCCA
 201 GCCCCGAGCC ATGATGAAGA CTTTGTCCAG CGGGAACTGC ACGCTCAGTG
 251 TGCCCGCCAA AAACTCATAC CGCATGGTGG TGCTGGGTGC CTCTCGGGTG
 301 GGCAAGAGCT CCATCGTGTC TCGCTTCCTC AATGGCCGCT TGAGGACCA
 351 GTACACACCC ACCATCGAGG ACTTCCACCG TAAGGTATAC AACATCCGCG
 401 GCGACATGTA CCAGCTCGAC ATCCTGGATA CCTCTGGCAA CCACCCCTTC
 451 CCCGCCATGC GCAGGCTGTC CATCCTCACA GGGGATGTCT TCATCCTGGT
 501 GTTCAGCCTG GATAACCGGG AGTCCTTCGA TGAGGTCAAG CGCCTTCAGA
 551 AGCAGATCCT GGAGGTCAAG TCCTGCCTGA AGAACAAGAC CAAGGAGGCG
 601 GCGGAGCTGC CCATGGTCAT CTGTGGCAAC AAGAACGACC ACGGCGAGCT
 651 GTGCCGCCAG GTGCCCACCA CCGAGGCCGA GCTGCTGGTG TCGGGCGACG
 701 AGAACTCCGC CTACTTCGAG GTGTCGGCCA AGAAGAACAC CAACGTGGAC
 751 GAGATGTTCT ACGTGCTCTT CAGCATGGCC AAGCTGCCAC ACGAGATGAG
 801 CCCCGCCCTG CATCGCAAGA TCTCCGTGCA GTACGGTGAC GCCTTCCACC
 851 CCAGGCCCTT CTGCATGCGC CGCGTCAAGG AGATGGACGC CTATGGCATG
 901 GTCTCGCCCT TCGCCCGCCG CCCCAGCGTC AACAGTGACC TCAAGTACAT
 951 CAAGGCCAAG GTCCTTCGGG AAGGCCAGGC CCGTGAGAGG GACAAGTGCA
1001 CCATCCAGTG AGCGAGGGAT GCTGGGCGG GGCTTGGCCA GTGCCTTCAG
1051 GGAGGTGGCC CCAGATGCCC ACTGTGCGCA TCTCCCCACC GAGGCCCCGG
1101 CAGCAGTCTT GTTCACAGAC CTTAGGCACC AGACTGGAGG CCCCCGGGCG
1151 CTGGCCTCCG CACATTCGTC TGCCTTCTCA CAGCTTTCCT GAGTCCGCTT
1201 GTCCACAGCT CCTTGGTGGT TTCATCTCCT CTGTGGGAGG ACACATCTCT
1251 GCAGCCTCAA GAGTTAGGCA GAGACTCAAG TTACACCTTC CTCTCCTGGG
1301 GTTGGAAGAA ATGTTGATGC CAGAGGGGTG AGGATTGCTG CGTCATATGG
1351 AGCCTCCTGG GACAAGCCTC AGGATGAAAA GGACACAGAA GGCCAGATGA
1401 GAAAGGTCTC CTCTCTCCTG GCATAACACC CAGCTTGGTT TGGGTGGCAG
1451 CTGGGAGAAC TTCTCTCCCA GCCCTGCAAC TCTTACGCTC TGGTTCAGCT
1501 GCCTCTGCAC CCCCTCCCAC CCCCAGCACA CACACAAGTT GGCCCCCAGC
1551 TGCGCCTGAC ATTGAGCCAG TGGACTCTGT GTCTGAAGGG GGCGTGGCCA
1601 CACCTCCTAG ACCACGCCCA CCACTTAGAC CACGCCCACC TCCTGACCGC
1651 GTTCCTCAGC CTCCTCTCCT AGGTCCCTCC GCCCGACAGT TGTGCTTTGT
1701 TGTGGTTGCA GCTGTTTTCG TGTCATGTAT AGTAGTAGAA ATGGAAATCA
1751 TTGTACTGTA AAAGCCTAGT GACTCCCTCC TTGGCCAGGC CCTCACCCAG
1801 TTCAGATCCA CGGCCTCCAC CCGGGACGCC TTCCTCCTCT GCTCCCAAAC
1851 AGGGTTCCG TGGCCTGTTT GCAGCTAGAC ATTGACCTCC GCCATTGAGC
1901 TCCACGGTTT ACAGACAATT GCACAAGCGT GGGGTGGGCA GGCCAGGACT
1951 GCTTTTTTTT AATGCTCCCA TTTCACAGAG GATACCACCG AGACTCGGAG
2001 GGGACACGAT GAGCACCAGG CCCCACCTTT GTCCCCTAGC AAATTCAGGG
2051 TACAGCTCCA CCTAGAACCA GGCTGCCCTC TACTGTGCTC GTTCCTCAAG
2101 CATTTATTAA GCACCTACTG GGTGCTGGGT TCACTGTGTC CTAGGAAACC
2151 AAGAGGGTCC CCAGTCCTGG CCTCTGCCCG CCCTGCTGC CCCACCACCT
2201 TCTGCACACA CAGCGGTGGG GAGGCGGGA GGAGCAGCTG GGACCCAGAA
2251 CTGAGCCTGG GAGGGATCCG ACAGAAAAGC TCAGGGCGGG TCTTCTCCTT
2301 GTGCCCGGGA TTGGGCTATG CTGGGTACCA CCATGTACTC AGGCATGGTG
2351 GGTTTTGAAC CCATAAACCA AAGGCCCTTG TCATCAGCTC TTAACAAGTA
2401 TATTTTGTAT TTTAATCTCT CTAAACATAT TGAAGTTTTA GGGCCCTAAG
2451 GAACCTTAGT GATCTTCTAT TGGGTCTTTC TGAGGTTCAG AGAGGGTAAG
2501 TAACTTCCTC CAGGTCACAC AGCAAGTCTG TGGGTGGCAG AAGCAAGCTA
2551 GCGCTGGGCA TTCAGTACAT ACCACGATGT GCTCCCTCTC TTGATGCTTG
2601 GCCCCTGGGG CCTTCAGGGC TTTGGGACAT CTTGTCCTCA ACCCTCTCCC
2651 TAGATCAGTC TGTGAGGGTC CCTGTAGATA TTGTGTACAC CATGCCCATG
2701 TATATACAAG TACACACAGA TGTACACACA GATGTACACA TGCTCCAGCC
2751 CCAGCTCTGC ATACCTGCAC CTGCACCCCA GCCTTGGCCC CTGCCTGCGT
2801 CTGTGCTCAA AGCAGCAGCT CCAACCCTGC CTCTGTCCCC TTCCCCACCC
2851 ACTGCCTGAG CCTTCTGAGC AGACCAGGTA CCTTGGCTGC ACCGGTGTGT
2901 GGCCCGCTCT CACCCAGGCA CAGCCCCGCC ACCATGGATC TCCGTGTACA
2951 CTATCAATAA AAGTGGGTTT GTTACAAAAA AAAAAAAAAA AAAAAAAAA
3001 AAAAAAAAAA AAAAAAAAAA AAAAAAAAAA AAAAAAAAAA AAAAAAAAA
3051 AAAAAAAAAA AAAAAAAAAA AAAAAAAAAA AA
```

FIGURE 1, page 1 of 3

FEATURES:
5'UTR:          1-210
Start Codon:    211
Stop Codon:     1009
3'UTR:          1012

5' UTR ANALYSIS:
Query=cDNA clone
Sbjct: genomic sequence

5' UTR Exon 1, non-coding
Score = 58.0 bits (29), Expect = 2e-10
 Identities = 29/29 (100%)
 Strand = Plus / Plus Query: 1     ggcgtcgccgcgcggggagaaagaagccg  29
             |||||||||||||||||||||||||||||
Sbjct: 1535  ggcgtcgccgcgcggggagaaagaagccg  1563

5' UTR Exon 2, non-coding
Score = 349 bits (176), Expect = 3e-98
 Identities = 176/176 (100%)
 Strand = Plus / Plus Query: 26    gccgcgcccagcccggcgtcccgagcagcgcaggggaggatccccgcgcagtgacccggg  85
             ||||||||||||||||||||||||||||||||||||||||||||||||||||||||||||
Sbjct: 2001  gccgcgcccagcccggcgtcccgagcagcgcaggggaggatccccgcgcagtgacccggg  2060

Query: 86    agccaccacagactctgggaggctcggcggctggagcagcaggcagctccccgcagctcc  145
             ||||||||||||||||||||||||||||||||||||||||||||||||||||||||||||
Sbjct: 2061  agccaccacagactctgggaggctcggcggctggagcagcaggcagctccccgcagctcc  2120

Query: 146   cggcgcttccaggcagctctctgagccgtgccagaggcccggcccgccattcccag  201
             |||||||||||||||||||||||||||||||||||||||||||||||||||||||
Sbjct: 2121  cggcgcttccaggcagctctctgagccgtgccagaggcccggcccgccattcccag  2176

Score =  563 bits (284), Expect = e-162
 Identities = 284/284 (100%)
 Strand = Plus / Plus 5' UTR Exon 3, Protein coding region begins at nucleotide 211

Query: 199   cagccccgagccatgatgaagactttgtccagcgggaactgcacgctcagtgtgcccgcc  258
             ||||||||||||||||||||||||||||||||||||||||||||||||||||||||||||
Sbjct: 7474  cagccccgagccatgatgaagactttgtccagcgggaactgcacgctcagtgtgcccgcc  7533

Homologous proteins:
Top BLAST Hits
                                                                    Score    E
CRA|18000005194969  /altid=gi|10047088  /def=ref|NP_055125.1|  sim...  538   e-152
CRA|18000005238449  /altid=gi|5059122   /def=gb|AAD38928.1|AF13440...  512   e-144
CRA|332000009620725 /altid=gi|8118457   /def=gb|AAF72997.1|AF2620...   342   2e-93
CRA|19000005232775  /altid=gi|7706359   /def=ref|NP_057168.1|  ras-... 342   2e-93
CRA|87000000006130  /altid=gi|7230768   /def=gb|AAF43090.1|AF23915... 342   3e-93
CRA|18000005090459  /altid=gi|6677673   /def=ref|NP_033052.1|  RAS,... 341   6e-93
CRA|89000000197633  /altid=gi|7295299   /def=gb|AAF50620.1|  (AE003... 228   8e-59
CRA|105000014645240 /altid=gi|10503969  /def=gb|AAG17979.1|AF177...   214   1e-54

FIGURE 1, page 2 of 3

```
BLAST dbEST hits:
gi|9345313  /dataset=dbest  /taxon=960...              880  0.0
gi|9335874  /dataset=dbest  /taxon=960...              846  0.0
gi|10143211 /dataset=dbest  /taxon=96...               821  0.0
gi|9335309  /dataset=dbest  /taxon=960...              813  0.0
gi|9150610  /dataset=dbest  /taxon=9606...             662  0.0
gi|10144589 /dataset=dbest  /taxon=96...               617  e-174
gi|9333908  /dataset=dbest  /taxon=960...              599  e-169
```

EXPRESSION INFORMATION FOR MODULATORY USE:
library source:
Expression information from BLAST dbEST hits:
gi|9345313   Placenta choriocarcinoma
gi|9335874   Uterus endometrium adenocarcinoma
gi|10143211  Skin melanotic melanoma
gi|9335309   Uterus endometrium adenocarcinoma
gi|9150610   Skin melanotic melanoma
gi|10144589  Skin melanotic melanoma
gi|9333908   Uterus endometrium adenocarcinoma Expression information from PCR-based tissue screening panels:
Human fetal whole brain FIGURE 1, page 3 of 3

```
  1 MMKTLSSGNC TLSVPAKNSY RMVVLGASRV GKSSIVSRFL NGRFEDQYTP
 51 TIEDFHRKVY NIRGDMYQLD ILDTSGNHPF PAMRRLSILT GDVFILVFSL
101 DNRESFDEVK RLQKQILEVK SCLKNKTKEA AELPMVICGN KNDHGELCRQ
151 VPTTEAELLV SGDENSAYFE VSAKKNTNVD EMFYVLFSMA KLPHEMSPAL
201 HRKISVQYGD AFHPRPFCMR RVKEMDAYGM VSPFARRPSV NSDLKYIKAK
251 VLREGQARER DKCTIQ
```

FEATURES:
Functional domains and key regions:
[1] PDOC00001 PS00001 ASN_GLYCOSYLATION
N-glycosylation site Number of matches: 2
    1    9-12   NCTL
    2  125-128  NKTK

[2] PDOC00004 PS00004 CAMP_PHOSPHO_SITE
cAMP- and cGMP-dependent protein kinase phosphorylation site Number of matches: 4
    1   84-87   RRLS
    2  174-177  KKNT
    3  202-205  RKIS
    4  236-239  RRPS

[3] PDOC00005 PS00005 PKC_PHOSPHO_SITE
Protein kinase C phosphorylation site

Number of matches: 2
    1   19-21   SYR
    2  172-174  SAK

[4] PDOC00006 PS00006 CK2_PHOSPHO_SITE
Casein kinase II phosphorylation site

Number of matches: 5
    1   51-54   TIED
    2  105-108  SFDE
    3  154-157  TEAE
    4  161-164  SGDE
    5  177-180  TNVD

[5] PDOC00007 PS00007 TYR_PHOSPHO_SITE
Tyrosine kinase phosphorylation site 220-228  RRVKEMDAY

[6] PDOC00266 PS00294 PRENYLATION
Prenyl group binding site (CAAX box)

263-266  CTIQ

[7] PDOC00016 PS00016 RGD
Cell attachment sequence 63-65  RGD

[8] PDOC00017 PS00017 ATP_GTP_A
ATP/GTP-binding site motif A (P-loop)

26-33  GASRVGKS

FIGURE 2, page 1 of 3

BLAST Alignment to Top Hit:
```
>CRA|18000005194969 /altid=gi|10047088 /def=ref|NP_055125.1| similar
        to mouse Ras, dexamethasone-induced 1; tumor endothelial
        marker 2 [Homo sapiens] /org=Homo sapiens /taxon=9606
        /dataset=nraa /length=278
        Length = 278

Score = 538 bits (1372), Expect = e-152
 Identities = 265/266 (99%), Positives = 265/266 (99%)

Query:   1   MMKTLSSGNCTLSVPAKNSYRMVVLGASRVGKSSIVSRFLNGRFEDQYTPTIEDFHRKVY   60
             MMKTLSSGNCTLSVPAKNSYRMVVLGASRVGKSSIVSRFLNGRFEDQYTPTIEDFHRKVY
Sbjct:  13   MMKTLSSGNCTLSVPAKNSYRMVVLGASRVGKSSIVSRFLNGRFEDQYTPTIEDFHRKVY   72

Query:  61   NIRGDMYQLDILDTSGNHPFPAMRRLSILTGDVFILVFSLDNRESFDEVKRLQKQILEVK  120
             NIRGDMYQLDILDTSGNHPFPAMRRLSILTGDVFILVFSLDNRESFDEVKRLQKQILEVK
Sbjct:  73   NIRGDMYQLDILDTSGNHPFPAMRRLSILTGDVFILVFSLDNRESFDEVKRLQKQILEVK  132

Query: 121   SCLKNKTKEAAELPMVICGNKNDHGELCRQVPTTEAELLVSGDENSAYFEVSAKKNTNVD  180
             SCLKNKTKEAAELPMVICGNKNDHGELCRQVPTTEAELLVSGDEN AYFEVSAKKNTNVD
Sbjct: 133   SCLKNKTKEAAELPMVICGNKNDHGELCRQVPTTEAELLVSGDENCAYFEVSAKKNTNVD  192

Query: 181   EMFYVLFSMAKLPHEMSPALHRKISVQYGDAFHPRPFCMRRVKEMDAYGMVSPFARRPSV  240
             EMFYVLFSMAKLPHEMSPALHRKISVQYGDAFHPRPFCMRRVKEMDAYGMVSPFARRPSV
Sbjct: 193   EMFYVLFSMAKLPHEMSPALHRKISVQYGDAFHPRPFCMRRVKEMDAYGMVSPFARRPSV  252

Query: 241   NSDLKYIKAKVLREGQARERDKCTIQ  266
             NSDLKYIKAKVLREGQARERDKCTIQ
Sbjct: 253   NSDLKYIKAKVLREGQARERDKCTIQ  278

Complete Amino Acid Sequence of gi|10047088 /def=ref|NP_055125.1| similar
        to mouse Ras, dexamethasone-induced 1; tumor endothelial
        marker 2 [Homo sapiens] /org=Homo sapiens /taxon=9606
        /dataset=nraa /length=278
        Length = 278
NOTE: UNDERLINED RESIDUES NOT PRESENT IN THE PROTEIN OF THE PRESENT INVENTION
        1 mpaslallqp rammktlssg nctlsvpakn syrmvvlgas rvgkssivsr flngrfedqy
       61 tptiedfhrk vynirgdmyq ldildtsgnh pfpamrrlsi ltgdvfilvf sldnresfde
      121 vkrlqkqile vksclknktk eaaelpmvic gnkndhgelc rqvptteael lvsgdencay
      181 fevsakkntn vdemfyvlfs maklphemsp alhrkisvqy gdafhprpfc mrrvkemday
      241 gmvspfarrp svnsdlkyik akvlregqar erdkctiq >CRA|18000005238449 /altid=gi|5059122 /def=gb|AAD38928.1|AF134409_1
        (AF134409) Rhes protein [Rattus norvegicus] /org=Rattus
        norvegicus /taxon=10116 /dataset=nraa /length=266
        Length = 266

Score = 512 bits (1304), Expect = e-144
 Identities = 252/266 (94%), Positives = 256/266 (95%)

Query:   1   MMKTLSSGNCTLSVPAKNSYRMVVLGASRVGKSSIVSRFLNGRFEDQYTPTIEDFHRKVY   60
             MMKTLSSGNCTL+VPAKNSYRMVVLGASRVGKSSIVSRFLNGRFEDQYTPTIEDFHRKVY
Sbjct:   1   MMKTLSSGNCTLNVPAKNSYRMVVLGASRVGKSSIVSRFLNGRFEDQYTPTIEDFHRKVY   60

Query:  61   NIRGDMYQLDILDTSGNHPFPAMRRLSILTGDVFILVFSLDNRESFDEVKRLQKQILEVK  120
             NI GDMYQLDILDTSGNHPFPAMRRLSILTGDVFILVFSLD+RESFDEVKRLQKQILEVK
Sbjct:  61   NIHGDMYQLDILDTSGNHPFPAMRRLSILTGDVFILVFSLDSRESFDEVKRLQKQILEVK  120

Query: 121   SCLKNKTKEAAELPMVICGNKNDHGELCRQVPTTEAELLVSGDENSAYFEVSAKKNTNVD  180
             SCLKNKTKEAAELPMVICGNKNDH ELCRQVP  EAELLVSGDEN AYFEVSAKKNTNV+
Sbjct: 121   SCLKNKTKEAAELPMVICGNKNDHSELCRQVPAMEAELLVSGDENCAYFEVSAKKNTNVN  180
```

```
Query: 181 EMFYVLFSMAKLPHEMSPALHRKISVQYGDAFHPRPFCMRRVKEMDAYGMVSPFARRPSV 240
            EMFYVLFSMAKLPHEMSPALH KISVQYGDAFHPRPFCMRR K  AYGMVSPFARRPSV
Sbjct: 181 EMFYVLFSMAKLPHEMSPALHHKISVQYGDAFHPRPFCMRRTKVAGAYGMVSPFARRPSV 240

Query: 241 NSDLKYIKAKVLREGQARERDKCTIQ 266
            NSDLKYIKAKVLREGQARERDKC+IQ
Sbjct: 241 NSDLKYIKAKVLREGQARERDKCSIQ 266
```

Hmmer search results (Pfam):

| Model | Description | Score | E-value | N |
|---|---|---|---|---|
| PF00071 | Ras family | 126.2 | 2.8e-36 | 1 |
| CE00060 | CE00060 rab_ras_like | 20.7 | 0.00013 | 2 |

Parsed for domains:

| Model | Domain | seq-f | seq-t | hmm-f | hmm-t | score | E-value |
|---|---|---|---|---|---|---|---|
| CE00060 | 1/2 | 22 | 52 .. | 26 | 56 .. | 16.9 | 0.0014 |
| CE00060 | 2/2 | 162 | 183 .. | 159 | 181 .. | 3.3 | 7.5 |
| PF00071 | 1/1 | 21 | 186 .. | 1 | 169 [. | 126.2 | 2.8e-36 |

FIGURE 2, page 3 of 3

```
   1 CTCTCTGACT CTTTGCCTCC TCTCTGACTC CCTGCCTCCT CTCTCTGTCT
  51 CCCTGCCTCC TCTGTCTGAC TCCCTGCCTC CCCTCTCTGT CTCACTGCCT
 101 CCTCTCTCTG ACTCTCTGCC TCCTCTCTCT GACTCCCTGC CTCCTCTCTC
 151 TGATTCCCTG CCTCTTTGAC CCTCTGCCTC CTCTCTTTGA CTCCCTGCCT
 201 CCTCTCTCCG ATTCTCTGCG TCTTTGACTC CCTGCCTCCT CTCTCTGACT
 251 CCCTGAAGCT CATTCAGTCA TTGCTATCAA CTCGTCTGTA CCAAGCTCTA
 301 GGCTGGAGGC TGGGCAGGGC AATGATGGAG ACAAATACTG TCCCTGGGAG
 351 CTTCTGGCCC CTTTCCCATC CTGTTTAGAC AGAAGTGACC GCCAGCAGAG
 401 TCAAGCTGTC TGCAGAAGGA CTTGGGGAGG GGGCTGTCAT GGGGTAGGGC
 451 TTCTTTCCCC CCATCTCTGC TGAAGGCCCA GGCTGGCTGA GACAGCCCCG
 501 GCAGAGACTG AGAAGGGCTC CCTGCTGTGG TCTGGCAGCC CCCTCTCCAC
 551 CCTCCTCTCT CTCATTTCCT GCCTCCCACA CGTATGCCCT GGGCACCTCA
 601 TCAGGGCTGC CCTAGGGGAG GGCCTCCTT GGCACAGCCC CTGGGCCAGT
 651 CAGGTGGTTG AGGCTGAGGA GAGAAGGTCC CAGAGTGGGG CTTCAGGCAA
 701 ACCCAAAGAC AGAGCCCTTT GCCATTTGAT GAATGCACAG ACCCTTTATT
 751 GAGCCCCTGC TCTGTTCATG GCATGGCAGT TTTGTGGGAT AAATTCAAAG
 801 ACAGCTTTAG GTGGGAGCTG GGTGGGGGAT GTGGGGGTCT TAGGCTTGAA
 851 CTACTACCCA GCCTCCTTTG TTAACCAAGT AGCTAGTCAC GTAGCCTTCT
 901 GAGCTCGGGG CAGACCACCT GGGATCAAAC CTCTCCTCTG CTGGTTACTG
 951 GCTGTGCAAC TGTAAGCAAG TAATTTAACC TCTCTGTGCC TCAGTTTCCT
1001 CATCTGTAAA TTGGAGAATA ACACCACCTG CTTTCTGGGG TTATGAAGGG
1051 AGAAATAGGT TAACATGTGT GCAGCACTTA GAACACTCTG GCATATTTTA
1101 GCTGCAAAAT GAATGCCAGC TATGATTATT TCTATACTTA GTGCGGGGCT
1151 TGGCACACTG CATGGGCTCA AGTGGCAGCA GTTGTCGTCC TTGTGGCTCC
1201 AGGCCTGGGG TCCGCCGTGT GCTGAGCTGG CTTATTGTGC ACGTCCCTTT
1251 GTGATTCATT CATCGAAGTC ACATTAGTAG CTTAGAAGTG ACCGTAGTGG
1301 GAGCATTTAC GCCATGGAAA TTGGCAATAG GGCTTTTAAC AAAGGTATTT
1351 TTGAGAGCCG GTTTCCTGCA CAGAGGCTGG TAGTTGGGCA GGGTGAGCAG
1401 ATCCAGATGT GTGCCAGGGA CTCGCACGCA GGCAATCTCT CCACCTCCAG
1451 TGCCCATCTC AGACCTTAGC TTCATGATAG CCAGGAAGCG ATGGTGTTGG
1501 AAAGCGCCTT GGGTCAATGG GCGAGGCACT CAAGGAAACC GACTTGGGGC
1551 ATCCTGGGGT GGGGACCGAG TTTGGGCACA TACAGCCCTT TGTGTGAATT
1601 TAAAAACAGT GCCTTTTCCT CTACACAAGA TGCCCTTTCG TCTGGGATAC
1651 AGCCCCACC TCTGGGATGC AGCCCCCACT TGCCCACCCA GCCATGCGCC
1701 TTGTGCAGTA TCCAACCTGC ACAACCTGTG GCAGCCTGTG GAAGACCGAG
1751 GGGATTGATA TTTCAGCAGG CCTGTGCCCA TTTGCAGTTC AGGGGCTGGA
1801 AAGCTCTCCT CTGGAGAGGG GAGGGATTCC TGCAAGGGTG AGGAGATCAG
1851 AGAGGCCTTC AGAGAGCAGG TGGCACTTGA GCCAGACCCT GAAACATAAG
1901 GGGAAGAGGG TGTTCTGCAG AGGGGTGGCA TGAGCAAAGG AGTGGAGGCT
1951 GATCTCAGCA GAGCTCAAAC TGACGAGGGT GACTGGGGTC AGGGGTTCTG
2001 GGGCGGGGAT TCTGGTGGGC GCTAAGGTAG GAAAGGAGGG AGGGCTGGGC
2051 TGTGAAGAGC CTTTGGGGTG AGCCTGGTGG AGCCTGCGGG TTTGCTTATA
2101 CAAGAGCTTG GATCCATGTC GGCCTCTTTC ATGAGGTCAA GAGGCTCCCA
2151 TAGAAAGCTC TGAGTTTGCC CCAGAACCAT AACCCTTGGA GATGGGAGGG
2201 AAGCTTGAGC CAGCCATGGG TCGTTCCCCA TTCCACATCC TCTACTCCGG
2251 GCCTCTGGGT CTCCTGGAGG CAAGTAAACA CCTAGGGCCT GGGAGGCAAA
2301 AATATCCGGG CAGGTCATGG AGCGGAGGGA GCCCGCCAGA TGCAGAGCAC
2351 AGGTCTAAAG GTGGGTCCTC CTGAGGTGGC TGCAGGAGCA ACCCCAGGCA
2401 TTGGGCTTGG AGCATGCGGT GTGGACATAG CCTTCCCTTC TTCCCAGGAG
2451 GGCTGAATGG CCACAGAACC ACCCCTGCC CCAGGCTTAA GAAATGCATG
2501 CTAGTGCCTT CCCCATGTCT TATCCTAGAA TCACAGGCTC CGGGAAAGCC
2551 AGATGGATGA ACCAGGGAAA GAACGGATTC TCACCATAGA TACCATTTTT
2601 GAGATTTCAC CATGTGCTGA GCCCTTTGCA ACAACTCTAT GAATTGGGCT
2651 CATTTTGCAG ATGAGAAAAG TGACTTCTAG AGAGGTTAAG CTACTAGCCC
2701 AAGATCAGTA GCTAGAGGCA AGGCAAGGAT TCAAATCCCA GGAGTCCGGT
2751 GCTTGCATAA ATGAAAGGAT GAATGAACGG ATATTGAGTG AGTAGTGGA
2801 TGAAGGAAGG AGTAAAGGAG AGGGCATGAA TGAATGAGAG GGTAGAACTC
2851 CAAGACCCCT TAGAACCTCG TCTGATGTTC CCATTTTACA GACAGAAAAC
2901 TGAGTCCTAG ACAGAGCCCT AGAGGAGGCC AAGAGGTGGT GGGGCCAGGT
2951 CGGGGGGGCC CTGATGCCTG CTTCTCTCGC TTTGTTGCAG CCCCGAGCCA
3001 TGATGAAGAC TTTGTCCAGC GGGAACTGCA CGCTCAGTGT GCCCGCCAAA
3051 AACTCATACC GCATGGTGGT GCTGGGTGCC CTCGGGTGG GCAAGAGCTC
3101 CATCGTGTCT CGCTTCCTCA ATGCCGCTT TGAGGACCAG TACACACCCA
```

FIGURE 3, page 1 of 6

```
3151 CCATCGAGGA CTTCCACCGT AAGGTATACA ACATCCGCGG CGACATGTAC
3201 CAGCTCGACA TCCTGGATAC CTCTGGCAAC CACCCCTTCC CCGCCATGCG
3251 CAGGCTGTCC ATCCTCACAG GTGAGGCCCA CTGGTGCCTG GGCTGGGGCG
3301 GCAGGGCCAG GGCATGGGTG CGGAGTGTGC TGGGCACTTG GCAGTTTGCA
3351 TAGACTTGCA TAGCCATCGT CTGAGACAGG CGTCATCCCT GCACAATGAG
3401 GCTCAGAGAG GTTTTGCCAT GTGCTGGAAA TAGTGATGAA GTCGGGGGCC
3451 CCGATTCCAT TCTGTTAGAC TCCAGATCGA TTACTCATGG CTGTCGGGGC
3501 CGCCTTCCAG ATCAGGAGCT GATACCAGCA TGCCCCAGGG ATATTCCTTT
3551 CTAGGGAACA GAATGATGCC CTGGCTGCTG CTTTCCTTCT CCGGAAGATG
3601 ACCCACCAGA GCTCCAGGGC CCAAGGTCAG TCCACGGGGC TCAGGTCTCC
3651 CACACCCCAG GCCTTTGCCA CCTCCTAGAG AGGTAAGGGC AGGACCCAGG
3701 CAGTGATCAC CAAAGGGAAG GGGGCTTGGT CATGGTCATA GTGATGGTGA
3751 TGGCACTAGC TGACACTTAT CAGAAGCTAT GGGCCTGGCC CTGTTCTTAG
3801 AGCTTGGCAT GTAGTTTTTT TTGAAACAGA GTCTCGCTCT GTCACCCAGG
3851 CTGGAGTGCA GTGGCGCGAT CTCGGCTCAC TGCAACCTCT GCCTCCCGGG
3901 TTCAAGCGAT TCTCCTGCCT CAGTCCCCCA AGTAGCTGGG ACTACAGGCA
3951 CGTGCCACCA TGCCCGGCTA ATTTTTTGTA TTTTTACTAG AGACGGGATT
4001 TCACCATGTT AGCCAGGATG GTCTCGATCT CCTGACCTCG TGATCTGCCT
4051 ACCTCAGCCT CCCAAAGTGC TGAGATTACA GGCGTCAGCC ACCGCGGCCA
4101 GCCAGCATGT AGTTATTTAA CCCTCACAGT AAATAGTTAT TCATTCCCTT
4151 TTTACAGGTG GGGAAACTGA AGCCCAGAGA GGTTAAGTAA CTCACTCCAG
4201 TGGTAGCACA GCTCGTAAAG GCAGTCTGCT TTTGTGCTTT CAGACAAAGC
4251 CATACCACAG CCTCTCAGCC CTGCTGGGAA GGGTGAGGAG GGACAGGGAG
4301 GTTGGGGGGA AGAAGGGGTG AGTGGAGCTG AGGGGCTGTG CCCTTGTTTA
4351 CACTGCATTA GCATGGTAGC TAAGAGGACA AGCCCGGGAC CCAGCACCTG
4401 GGTGTGAGCC CTGGTTCCGC TGCTTCCTGG CTTTGTACCT CGAGGCAAGG
4451 GATTTTATCT CCTTGTGTCT CAGCACTCTC ATCTGTAAGA CTGCACCACA
4501 TCAACACTCA TCCTAAAGGG ACTGTGAGAC TTAAATGAAT GAATATATGT
4551 AAGGCGCTTG GTGAGCAGAT AGTAAATGCA CAATAAATCC CCAAGTCTTC
4601 TGTTGAGTCA GCATTTGCAA GTGGGCCTGC TACGGGTTAC ACGATCATTT
4651 CCCAAGTCAC GCCCCTGAAG TTGCTGAGCA GGGATAAGGG AAGGAGTGAG
4701 CAGGCAACTC TCTAGGCATC ATTCAGATAA CCCCCCAACT GAGGTACTTC
4751 TATACAGAGA AACCCATGCC ACTCCCAGCC CTGCTGCCGC CTTGAGGCCA
4801 AGACTGAGGC TGCGGGGTGG CCCCTCCTTG AGTGCTTTCT CTTCCAGGCT
4851 GGCTTTTCCG AGCATCTGAC CCAGACAGCA GTCAAGTTCT CCGCTCCACC
4901 CCGAGTTTTG GAGAAGGGGC ATGTAGATAG GAGAGCCCTG GGTCGACCTG
4951 TGTTCGAATC CTTGCTGGGC CTCTTGGCTT AAATGTGTGA CCAGAGGCAC
5001 ATGCATCCTG TCTGAGTCTC AGCCTCCCCA GCCACACAGT GGGCTTAACC
5051 TCATACCCCG CAGGGAGGCT GTGAGGACTG CAAGAAGGCT TGTGGCGGGA
5101 GCTTCCAGCA CGTGACGGGT ATTGCATTGG TGTCAGCTCC CCCAGCCTTG
5151 GGGAGGGGAC TGGGTACCCG CTGCAATGAA TAAGGCTAAT GACAGAGGGA
5201 AGGAGAGGGG AGATGTAGAG AGGAAGCACA TGCATATTTT CAGCATTAAT
5251 TTTCAGTGAC ACAAGTAATA CCCAAACACA CCCTCCTGCA AACGCTACAG
5301 ATAAAGCTAA TGCCCCTTTG ACCCATGTCC CCAATCCCAG GCTCCTGCCC
5351 CTGCCCCGGA GGTGGCCACC CTGGCAGTCT GGCATGGAGC CTTCCGGGCC
5401 TCCGTGACTA CACCGGCATT CGTATTTGTA TCCCCACAAT GGAGAGTATT
5451 TTTGTCTGTC TCTTTTTTAT GGCGCATATC ATTCTGAGCA CAGCTGTCTG
5501 ATGCTTGTTT TTTTTTCACA CACCAACCCG TGCCTCATTT TCCAACCTGG
5551 TGGAACCTCA TTTTTTCAAC CTCATTTTCC TGCTGCTCAG GAAATTCTGA
5601 AAGCCATTAA TTCCACTGCC AGTCTTCTT CCAGCTGCCA GACGGGCCGA
5651 TCTCTGATGC TTGGCATCGC AGTCTCGCAT TTGAATATGT CAAGGCCACG
5701 AGTCCTCAGG GGCCCCGGAT TAGCCTAACG GGATGGGGTT TGGCAGCCCA
5751 AGCAGGAAGA GTTGCCAAGC TGACGCTGCC TCGCAAGTGC CTTTCAGAAG
5801 AGCCCACACT GCAGTTCCCT CCATCACCTC CCATCCATTC AGGCTTCCTT
5851 GGTTAACACT GACTGTGTGC CAGGCCCTGG GGAGACCAGG ACGAGTGGGT
5901 GATGGAACCC TTCTCTGTGC CCGAGCTGTT TGGAGCACAC CTTTGATCTG
5951 GACACCATTC TGAATGTGCC ATGTGCCATT AAATGGGGGT AAATGATGTG
6001 CTCTGGGGGT GCAGAGGAAG GTGGCAGCCA TTCTGCCAGA AGCTGGAACT
6051 GGTTGCTTCT CTTCTCAAGA ATTTGGGCCA ATTGCTGATT CCTCTGGGCC
6101 TCAGTTTCCT CATCTGTGAG ACAGGGATCT TGTCACACCA CAAGGCTATC
6151 AAGAGTTTGA GCAAAAGTGG TTGGACGCAG TGGCTCATGC CTGTAATCCC
6201 AGCTCTTTGG GAGGCCGAGG TGGGCAGATC TCTTGAGGTC AGGAGTTCAA
6251 GACCAGCCTG GCTAACACAG TGAAACACCG TCTCTACTAA AAAATACAAA
```

FIGURE 3, page 2 of 6

```
6301 AAATTAGCCA GGTGTGGTGA TGGGCACCTG TAATCCCAGT TACTCGGGAG
6351 GCTGAGGCAG GAGAATCTCT TGAACCCAGG AGGTGGAGGT TGCAGTGAGC
6401 TGAGATCTTG CCATTGCATT CCAGGCTGGG CAACAAGAGT GAAACTCTGT
6451 CTCAGAAAAT AAATAAATAA ATAAATAAAA AATAGCTAGG CATGGTGACA
6501 GGCGCCTGTA ATCCCAGCTG CTCCAGAGGC TGAGGCAGGA GAATCGCTTA
6551 AACCCAGGAG GTGGAAGTTG CAGTGAGCCA AGATCACACC ACTGCACTCC
6601 AGCCTGGGCC ACAGAGAAAG ACTCCATCTC AAAAAAAAAA AAAAAAAAAA
6651 AAAAAGTTTA AGCAAAAGTG AGGAAGGTGC TTATTAAAAG CTGGAAATCA
6701 GGATGGAGGT ACCAGTCCAG ACAGCCTCCC CACCACCCCA CCGTCTCCAC
6751 AGCAGCCCCT GTTTCAGATT CACAAGCCTG CCTTGAGTGA TGCAGTGAGT
6801 TATCCTGGAG GCAGTGTGGG CCTTGGAGGC CAGCACTCAC TTTTTCATCC
6851 TATGATTTAT TTGAGAAGCA GAGAGCACCT ACCGGGTGCC AGGAACGAGC
6901 TAGGTGAGAA CAGAATCAGG TAGAAATCTC AGCCTAGCCA CACGGAAGCT
6951 GTGTGATCTT GGGCAGGCTG CATACCCTTT CTGAGCCTCA GTTTGCTCAC
7001 CTGTAATGCA AAGGTAACAA AATCTTGACA GAGGCATAGT GAGGAATCAA
7051 GAGAACAACG GGCCTGGAGC ATACACCCAG TGCTTAGCCC CCAGTAGGCC
7101 CTCACTCTCA TCATTACTGA CACCTGAGGT CACTGAGCAT GTGCCACTGT
7151 CCATTCATTA TCTTGCATAA CTCCCAAAAT CATCCTGCAA GGTAATATTT
7201 CATCTTCATG AAACAGACAG AGAAACTGAG GTTACAGAGG TTTCGTGATC
7251 TGCCCAAGTC TGCTGGCAGC TAAGCGGATG AGGCCAGATG CAAACTAGGC
7301 ATTGAGCAAG ACAGGCAGGA CCCCTGCTCT CATAGAAATG ATTTTTATTA
7351 TTATCTGAAC ACAGTCCACA CAAGTGACCT ACCCCTCTCC AGCCCTGCAA
7401 AGAAATGTGA AGTGAGTTAA CTGTATTTGA ACCAAGTGGT CCACGTGTTA
7451 GCTATGCGAC TGTGAACAGG GGCTTCAACC CCTCAGCCT CAGTTTCCTG
7501 TCCTGGAAAA TAATCGCAGG GAGAATAATC GCAGCTACCC CGAAGAGTCG
7551 CTGTGTAGGT TAAAGCAGTT ATGCCGCATA ACTGCTTCAG GGCACCTGTG
7601 ACTCCCAGCT CTTAGGGCTG ATGTTCTGTG GCCAGAGGAG GGCAGGGGTT
7651 GCAGCTGGCC GGTGAACTCA CTACCTGGGC TCTCTCCCTG CAGGGGATGT
7701 CTTCATCCTG GTGTTCAGCC TGGATAACCG GGAGTCCTTC GATGAGGTCA
7751 AGCGCCTTCA GAAGCAGATC CTGGAGGTCA AGTCCTGCCT GAAGAACAAG
7801 ACCAAGGAGG CGGCGGAGCT GCCCATGGTC ATCTGTGGCA ACAAGAACGA
7851 CCACGGCGAG CTGTGCCGCC AGGTGCCCAC CACCGAGGCC GAGCTGCTGG
7901 TGTCGGGCGA CGAGAACTGC GCCTACTTCG AGGTGTCGGC CAAGAAGAAC
7951 ACCAACGTGG ACGAGATGTT CTACGTGCTC TTCAGCATGG CCAAGCTGCC
8001 ACACGAGATG AGCCCCGCCC TGCATCGCAA GATCTCCGTG CAGTACGGTG
8051 ACGCCTTCCA CCCCAGGCCC TTCTGCATGC GCCGCGTCAA GGAGATGGAC
8101 GCCTATGGCA TGGTCTCGCC CTTCGCCCGC CGCCCCAGCG TCAACAGTGA
8151 CCTCAAGTAC ATCAAGGCCA AGGTCCTTCG GAAGGCCAG GCCCGTGAGA
8201 GGGACAAGTG CACCATCCAG TGAGCGAGGG ATGCTGGGGC GGGGCTTGGC
8251 CAGTGCCTTC AGGGAGGTGG CCCCAGATGC CCACTGTGCG CATCTCCCCA
8301 CCGAGGCCCC GGCAGCAGTC TTGTTCACAG ACCTTAGGCA CCAGACTGGA
8351 GGCCCCCGGG CGCTGGCCTC CGCACATTCG TCTGCCTTCT CACAGCTTTC
8401 CTGAGTCCGC TTGTCCACAG CTCCTTGGTG GTTTCATCTC CTCTGTGGGA
8451 GGACACATCT CTGCAGCCTC AAGAGTTAGG CAGAGACTCA AGTTACACCT
8501 TCCTCTCCTG GGGTTGGAAG AAATGTTGAT GCCAGAGGGG TGAGGATTGC
8551 TGCGTCATAT GGAGCCTCCT GGGACAAGCC TCAGGATGAA AAGGACACAG
8601 AAGGCCAGAT GAGAAAGGTC TCCTCTCTCC TGGCATAACA CCCAGCTTGG
8651 TTTGGGTGGC AGCTGGGAGA ACTTCTCTCC CAGCCCTGCA ACTCTTACGC
8701 TCTGGTTCAG CTGCCTCTGC ACCCCCTCCC ACCCCCAGCA CACACACAAG
8751 TTGGCCCCCA GCTGCGCCTG ACATTGAGCC AGTGGACTCT GTGTCTGAAG
8801 GGGGCGTGGC CACACCTCCT AGACCACGCC CACCACTTAG ACCACGCCCA
8851 CCTCCTGACC GCGTTCCTCA GCCTCCTCTC CTAGGTCCCT CCGCCCGACA
8901 GTTGTGCTTT GTTGTGGTTG CAGCTGTTTT CGTGTCATGT ATAGTAGTAG
8951 AAATGGAAAT CATTGTACTG TAAAAGCCTA GTGACTCCCT CCTTGGCCAG
9001 GCCCTCACCC AGTTCAGATC CACGGCCTCC ACCCGGGACG CCTTCCTCCT
9051 CTGCTCCCAA ACAGGGTTTC CGTGGCCTGT TTGCAGCTAG ACATTGACCT
9101 CCGCCATTGA GCTCCACGGT TTACAGACAA TTGCACAAGC GTGGGGTGGG
9151 CAGGCCAGGA CTGCTTTTTT TTAATGCTCC CATTTCACAG AGGATACCAC
9201 CGAGACTCGG AGGGGACACG ATGAGCACCA GGCCCCACCT TTGTCCCCTA
9251 GCAAATTCAG GGTACAGCTC CACCTAGAAC CAGGCTGCCC TCTACTGTGC
9301 TCGTTCCTCA AGCATTTATT AAGCACCTAC TGGGTGCTGG GTTCACTGTG
9351 TCCTAGGAAA CCAAGAGGGT CCCCAGTCCT GGCCTCTGCC CGCCCCTGCT
9401 GCCCCACCAC CTTCTGCACA CACAGCGGTG GGGAGGCGGG GAGGAGCAGC
```

FIGURE 3, page 3 of 6

```
 9451 TGGGACCCAG AACTGAGCCT GGGAGGGATC CGACAGAAAA GCTCAGGGCG
 9501 GGTCTTCTCC TTGTGCCCGG GATTGGGCTA TGCTGGGTAC CACCATGTAC
 9551 TCAGGCATGG TGGGTTTTGA ACCCATAAAC CAAAGGCCCT TGTCATCAGC
 9601 TCTTAACAAG TATATTTTGT ATTTTAATCT CTCTAAACAT ATTGAAGTTT
 9651 TAGGGCCCTA AGGAACCTTA GTGATCTTCT ATTGGGTCTT TCTGAGGTTC
 9701 AGAGAGGGTA AGTAACTTCC TCCAGGTCAC ACAGCAAGTC TGTGGGTGGC
 9751 AGAAGCAAGC TAGCGCTGGG CATTCAGTAC ATACCACGAT GTGCTCCCTC
 9801 TCTTGATGCT TGGCCCCTGG GGCCTTCAGG GCTTTGGGAC ATCTTGTCCT
 9851 CAACCCTCTC CCTAGATCAG TCTGTGAGGG TCCCTGTAGA TATTGTGTAC
 9901 ACCATGCCCA TGTATATACA AGTACACACA GATGTACACA CAGATGTACA
 9951 CATGCTCCAG CCCCAGCTCT GCATACCTGC ACCTGCACCC CAGCCTTGGC
10001 CCCTGCCTGC GTCTGTGCTC AAAGCAGCAG CTCCAACCCT GCCTCTGTCC
10051 CCTTCCCCAC CCACTGCCTG AGCCTTCTGA GCAGACCAGG TACCTTGGCT
10101 GCACCGGTGT GTGGCCCGCT CTCACCCAGG CACAGCCCCG CCACCATGGA
10151 TCTCCGTGTA CACTATCAAT AAAAGTGGGT TTGTTACAAA GCCGTGTCCT
10201 TGCCCATGTG TATTTTTTGT ATTTCCAAGA GGAGGTGTGC CCCTTTCCAG
10251 ACCAAAGCTG GCCTTTCCCT CCCAAAATGC ACCTGCCGTG TACCCTGGCC
10301 CTGAGGGTCA GCACTGAGTC CACCTTCAAG TGTAAGTGTG GGGAGAGGGG
10351 GATAAGTCCC CCAGATGGAA GGTGATGCCC TCCTTCAGCC TGGCCCTCCT
10401 GGGTCCTCCG GGTGTGTGTA CCGAGGTGTC TGTGTCCACA AGAAGGGGC
10451 CCCCGTGGAC CATTAGCTCC AGGAGGATCT CCGTGTCTGA GTTCTTTGTG
10501 ATTCCTGTAC AGCAGCAATT TCACCCGCAG GGGACAGTTG GCAATCTCTG
10551 GAAACCTTTT CCAAGCCTGG GGCTGGGGCT GCTACTCTCA TCTGGTGGGT
10601 GGAGGCCAGG GACACCATTC AGTATCCTCC AACGCACAGG ATGCCCCTCC
10651 ACCCCCACCC CACTGAGAAT TATCTGGCCT CAAATGCCAA GCGTGGGCAG
10701 CCTTACTTAG ACTCACCCCA GGGGCTGGGA CACGCCCCA CCTGCGTGTG
10751 ATGGATTTGT TGGACCACAT TCTGGACGGA ACCCACAGCA TAAGCACTCC
10801 TGTGAAGTGA GACAGGATGT GGGTGAGGAT GGAAAGTGGA GGCTGAGGGA
10851 GAAGGTCTGG GCCCTGACCA ACACGGAATG TGCCCCCTGG GACTGAGAGG
10901 CTTCCCTGGG CAGAGGGAAA GGAGGAAGTC AGTGAGGTAA AATACTCCCT
10951 GTGTGTTTTA CCCAGCGAGT CTCACGCCAT CCTATCACCC AGCCCCGAGG
11001 GAAGCCCACT CATGTTCACC CCATCTGAGC ATTTAGGCTC AGAGAGCTCA
11051 ATATCTTGTC CAAGATGGCA CAGCTGGTGA AGTGGCAGAT CAGAGATTCA
11101 ACACCAGAGG CTGTCTGATT TCCGTCTGGC TGAAGAAAGA TTTTGCATCA
11151 GGGAGGTGGA AACCATCTGT GCTTTTGATC AGCAAATGCC ACCAGCAGGA
11201 TCAGGGAGCC AGGCCATAAA G
```

FEATURES:
Start: 3000
Exon: 3000-3270
Intron: 3271-7693
Exon: 7694-8220
Stop: 8221

CHROMOSOME MAP POSITION:
Chromosome 22

ALLELIC VARIANTS (SNPs):
DNA

| Position | Major | Minor | Domain |
|---|---|---|---|
| 3951 | C | T | Intron |
| 4127 | C | T | Intron |
| 4157 | G | A | Intron |
| 4513 | C | T | Intron |
| 6894 | C | A | Intron |
| 8409 | G | C | Beyond ORF(3') |
| 8437 | T | G | Beyond ORF(3') |
| 8579 | T | C | Beyond ORF(3') |
| 10292 | A | G | Beyond ORF(3') |
| 10792 | A | G | Beyond ORF(3') |

Context:

FIGURE 3, page 4 of 6

| DNA Position | |
|---|---|
| 3951 | CACACCCCAGGCCTTTGCCACCTCCTAGAGAGGTAAGGGCAGGACCCAGGCAGTGATCAC
CAAAGGGAAGGGGGCTTGGTCATGGTCATAGTGATGGTGATGGCACTAGCTGACACTTAT
CAGAAGCTATGGGCCTGGCCCTGTTCTTAGAGCTTGGCATGTAGTTTTTTTTGAAACAGA
GTCTCGCTCTGTCACCCAGGCTGGAGTGCAGTGGCGCGATCTCGGCTCACTGCAACCTCT
GCCTCCCGGGTTCAAGCGATTCTCCTGCCTCAGTCCCCAAGTAGCTGGGACTACAGGCA
[C,T]
GTGCCACCATGCCCGGCTAATTTTTTGTATTTTTACTAGAGACGGGATTTCACCATGTTA
GCCAGGATGGTCTCGATCTCCTGACCTCGTGATCTGCCTACCTCAGCCTCCCAAAGTGCT
GAGATTACAGGCGTCAGCCACCGCGGCCAGCCAGCATGTAGTTATTTAACCCTCACAGTA
AATAGTTATTCATTCCCTTTTTACAGGTGGGGAAACTGAAGCCCAGAGAGGTTAAGTAAC
TCACTCCAGTGGTAGCACAGCTCGTAAAGGCAGTCTGCTTTTGTGCTTTCAGACAAAGCC |
| 4127 | CAGAGTCTCGCTCTGTCACCCAGGCTGGAGTGCAGTGGCGCGATCTCGGCTCACTGCAAC
CTCTGCCTCCCGGGTTCAAGCGATTCTCCTGCCTCAGTCCCCAAGTAGCTGGGACTACA
GGCACGTGCCACCATGCCCGGCTAATTTTTGTATTTTTACTAGAGACGGGATTTCACCA
TGTTAGCCAGGATGGTCTCGATCTCCTGACCTCGTGATCTGCCTACCTCAGCCTCCCAAA
GTGCTGAGATTACAGGCGTCAGCCACCGCGGCCAGCCAGCATGTAGTTATTTAACCCTCA
[C,T]
AGTAAATAGTTATTCATTCCCTTTTTACAGGTGGGGAAACTGAAGCCCAGAGAGGTTAAG
TAACTCACTCCAGTGGTAGCACAGCTCGTAAAGGCAGTCTGCTTTTGTGCTTTCAGACAA
AGCCATACCACAGCCTCTCAGCCCTGCTGGGAAGGGTGAGGAGGGACAGGGAGGTTGGGG
GGAAGAAGGGGTGAGTGGAGCTGAGGGGCTGTGCCCTTGTTTACACTGCATTAGCATGGT
AGCTAAGAGGACAAGCCCGGGACCCAGCACCTGGGTGTGAGCCCTGGTTCCGCTGCTTCC |
| 4157 | TGCAGTGGCGCGATCTCGGCTCACTGCAACCTCTGCCTCCCGGGTTCAAGCGATTCTCCT
GCCTCAGTCCCCAAGTAGCTGGGACTACAGGCACGTGCCACCATGCCCGGCTAATTTTT
TGTATTTTTACTAGAGACGGGATTTCACCATGTTAGCCAGGATGGTCTCGATCTCCTGAC
CTCGTGATCTGCCTACCTCAGCCTCCCAAAGTGCTGAGATTACAGGCGTCAGCCACCGCG
GCCAGCCAGCATGTAGTTATTTAACCCTCACAGTAAATAGTTATTCATTCCCTTTTTACA
[G,A]
GTGGGGAAACTGAAGCCCAGAGAGGTTAAGTAACTCACTCCAGTGGTAGCACAGCTCGTA
AAGGCAGTCTGCTTTTGTGCTTTCAGACAAAGCCATACCACAGCCTCTCAGCCCTGCTGG
GAAGGGTGAGGAGGGACAGGGAGGTTGGGGGGAAGAAGGGGTGAGTGGAGCTGAGGGGCT
GTGCCCTTGTTTACACTGCATTAGCATGGTAGCTAAGAGGACAAGCCCGGGACCCAGCAC
CTGGGTGTGAGCCCTGGTTCCGCTGCTTCCTGGCTTTGTACCTCGAGGCAAGGGATTTTA |
| 4513 | TCGTAAAGGCAGTCTGCTTTTGTGCTTTCAGACAAAGCCATACCACAGCCTCTCAGCCCT
GCTGGGAAGGGTGAGGAGGGACAGGGAGGTTGGGGGGAAGAAGGGGTGAGTGGAGCTGAG
GGGCTGTGCCCTTGTTTACACTGCATTAGCATGGTAGCTAAGAGGACAAGCCCGGGACCC
AGCACCTGGGTGTGAGCCCTGGTTCCGCTGCTTCCTGGCTTTGTACCTCGAGGCAAGGGA
TTTTATCTCCTTGTGTCTCAGCACTCTCATCTGTAAGACTGCACCACATCAACACTCATC
[C,T]
TAAAGGGACTGTGAGACTTAAATGAATGAATATATGTAAGGCGCTTGGTGAGCAGATAGT
AAATGCACAATAAATCCCCAAGTCTTCTGTTGAGTCAGCATTTGCAAGTGGGCCTGCTAC
GGGTTACACGATCATTTCCCAAGTCACGCCCCTGAAGTTGCTGAGCAGGGATAAGGGAAG
GAGTGAGCAGGCAACTCTCTAGGCATCATTCAGATAACCCCCCAACTGAGGTACTTCTAT
ACAGAGAAACCCATGCCACTCCCAGCCCTGCTGCCGCCTTGAGGCCAAGACTGAGGCTGC |
| 6894 | GCACTCCAGCCTGGGCCACAGAGAAAGACTCCATCTCAAAAAAAAAAAAAAAAAAAAAAA
AAGTTTAAGCAAAAGTGAGGAAGGTGCTTATTAAAAGCTGGAAATCAGGATGGAGGTACC
AGTCCAGACAGCCTCCCCACCACCCCACCGTCTCCACAGCAGCCCCTGTTTCAGATTCAC
AAGCCTGCCTTGAGTGATGCAGTGAGTTATCCTGGAGGCAGTGTGGGCCTTGGAGGCCAG
CACTCACTTTTTCATCCTATGATTTATTTGAGAAGCAGAGAGCACCTACCGGGTGCCAGG
[C,A]
ACGAGCTAGGTGAGAACAGAATCAGGTAGAAATCTCAGCCTAGCCACACGGAAGCTGTGT
GATCTTGGGCAGGCTGCATACCCTTTCTGAGCCTCAGTTTGCTCACCTGTAATGCAAAGG
TAACAAAATCTTGACAGAGGCATAGTGAGGAATCAAGAGAACAACGGGCCTGGAGCATAC
ACCCAGTGCTTAGCCCCCAGTAGGCCCTCACTCTCATCATTACTGACACCTGAGGTCACT
GAGCATGTGCCACTGTCCATTCATTATCTTGCATAACTCCCAAAATCATCCTGCAAGGTA |

FIGURE 3, page 5 of 6

8409    CATGGTCTCGCCCTTCGCCCGCCGCCCCAGCGTCAACAGTGACCTCAAGTACATCAAGGC
        CAAGGTCCTTCGGGAAGGCCAGGCCCGTGAGAGGGACAAGTGCACCATCCAGTGAGCGAG
        GGATGCTGGGGCGGGGCTTGGCCAGTGCCTTCAGGGAGGTGGCCCCAGATGCCCACTGTG
        CGCATCTCCCCACCGAGGCCCCGGCAGCAGTCTTGTTCACAGACCTTAGGCACCAGACTG
        GAGGCCCCCGGGCGCTGGCCTCCGCACATTCGTCTGCCTTCTCACAGCTTTCCTGAGTCC
        [G,C]
        CTTGTCCACAGCTCCTTGGTGGTTTCATCTCCTCTGTGGGAGGACACATCTCTGCAGCCT
        CAAGAGTTAGGCAGAGACTCAAGTTACACCTTCCTCTCCTGGGGTTGGAAGAAATGTTGA
        TGCCAGAGGGGTGAGGATTGCTGCGTCATATGGAGCCTCCTGGGACAAGCCTCAGGATGA
        AAAGGACACAGAAGGCCAGATGAGAAAGGTCTCCTCTCTCCTGGCATAACACCCAGCTTG
        GTTTGGGTGGCAGCTGGGAGAACTTCTCTCCCAGCCCTGCAACTCTTACGCTCTGGTTCA

8437    AGCGTCAACAGTGACCTCAAGTACATCAAGGCCAAGGTCCTTCGGGAAGGCCAGGCCCGT
        GAGAGGGACAAGTGCACCATCCAGTGAGCGAGGGATGCTGGGGCGGGGCTTGGCCAGTGC
        CTTCAGGGAGGTGGCCCCAGATGCCCACTGTGCGCATCTCCCCACCGAGGCCCCGGCAGC
        AGTCTTGTTCACAGACCTTAGGCACCAGACTGGAGGCCCCCGGGCGCTGGCCTCCGCACA
        TTCGTCTGCCTTCTCACAGCTTTCCTGAGTCCGCTTGTCCACAGCTCCTTGGTGGTTTCA
        [T,G]
        CTCCTCTGTGGGAGGACACATCTCTGCAGCCTCAAGAGTTAGGCAGAGACTCAAGTTACA
        CCTTCCTCTCCTGGGGTTGGAAGAAATGTTGATGCCAGAGGGGTGAGGATTGCTGCGTCA
        TATGGAGCCTCCTGGGACAAGCCTCAGGATGAAAAGGACACAGAAGGCCAGATGAGAAAG
        GTCTCCTCTCTCCTGGCATAACACCCAGCTTGGTTTGGGTGGCAGCTGGGAGAACTTCTC
        TCCCAGCCCTGCAACTCTTACGCTCTGGTTCAGCTGCCTCTGCACCCCCTCCCACCCCCA

8579    GCCCACTGTGCGCATCTCCCCACCGAGGCCCCGGCAGCAGTCTTGTTCACAGACCTTAGG
        CACCAGACTGGAGGCCCCCGGGCGCTGGCCTCCGCACATTCGTCTGCCTTCTCACAGCTT
        TCCTGAGTCCGCTTGTCCACAGCTCCTTGGTGGTTTCATCTCCTCTGTGGGAGGACACAT
        CTCTGCAGCCTCAAGAGTTAGGCAGAGACTCAAGTTACACCTTCCTCTCCTGGGGTTGGA
        AGAAATGTTGATGCCAGAGGGGTGAGGATTGCTGCGTCATATGGAGCCTCCTGGGACAAG
        [T,C]
        CTCAGGATGAAAAGGACACAGAAGGCCAGATGAGAAAGGTCTCCTCTCTCCTGGCATAAC
        ACCCAGCTTGGTTTGGGTGGCAGCTGGGAGAACTTCTCTCCCAGCCCTGCAACTCTTACG
        CTCTGGTTCAGCTGCCTCTGCACCCCCTCCCACCCCCAGCACACACACAAGTTGGCCCCC
        AGCTGCGCCTGACATTGAGCCAGTGGACTCTGTGTCTGAAGGGGCGTGGCCACACCTCC
        TAGACCACGCCCACCACTTAGACCACGCCCACCTCCTGACCGCGTTCCTCAGCCTCCTCT

10292   AGCCTTGGCCCCTGCCTGCGTCTGTGCTCAAAGCAGCAGCTCCAACCCTGCCTCTGTCCC
        CTTCCCCACCCACTGCCTGAGCCTTCTGAGCAGACCAGGTACCTTGGCTGCACCGGTGTG
        TGGCCCGCTCTCACCCAGGCACAGCCCCGCCACCATGGATCTCCGTGTACACTATCAATA
        AAAGTGGGTTTGTTACAAAGCCGTGTCCTTGCCCATGTGTATTTTTTGTATTTCCAAGAG
        GAGGTGTGCCCCTTTCCAGACCAAAGCTGGCCTTTCCCTCCCAAAATGCACCTGCCGTGT
        [A,G]
        CCCTGGCCCTGAGGGTCAGCACTGAGTCCACCTTCAAGTGTAAGTGTGGGGAGAGGGGGA
        TAAGTCCCCCAGATGGAAGGTGATGCCCTCCTTCAGCCTGGCCCTCCTGGGTCCTCCGGG
        TGTGTGTACCGAGGTGTCTGTGTCCACAAAGAAGGGGCCCCCGTGGACCATTAGCTCCAG
        GAGGATCTCCGTGTCTGAGTTCTTTGTGATTCCTGTACAGCAGCAATTTCACCCGCAGGG
        GACAGTTGGCAATCTCTGGAAACCTTTTCCAAGCCTGGGGCTGGGGCTGCTACTCTCATC

10792   TTCTTTGTGATTCCTGTACAGCAGCAATTTCACCCGCAGGGGACAGTTGGCAATCTCTGG
        AAACCTTTTCCAAGCCTGGGGCTGGGGCTGCTACTCTCATCTGGTGGGTGGAGGCCAGGG
        ACACCATTCAGTATCCTCCAACGCACACCATGCCCTCCACCCCCACCCCACTGAGAATT
        ATCTGGCCTCAAATGCCAAGCGTGGGCAGCCTTACTTAGACTCACCCCAGGGGCTGGGAC
        ACGCCCCACCTGCGTGTGATGGATTTGTTGGACCACATTCTGGACGGAACCCACAGCAT
        [A,G]
        AGCACTCCTGTGAAGTGAGACAGGATGTGGGTGAGGATGGAAAGTGGAGGCTGAGGGAGA
        AGGTCTGGGCCCTGACCAACACGGAATGTGCCCCCTGGGACTGAGAGGCTTCCCTGGGCA
        GAGGGAAAGGAGGAAGTCAGTGAGGTAAAATACTCCCTGTGTGTTTTACCCAGCGAGTCT
        CACGCCATCCTATCACCCAGCCCCGAGGGAAGCCCACTCATGTTCACCCCATCTGAGCAT
        TTAGGCTCAGAGAGCTCAATATCTTGTCCAAGATGGCACAGCTGGTGAAGTGGCAGATCA

FIGURE 3, page 6 of 6

SEQUENCE LISTING

<160> NUMBER OF SEQ ID NOS: 9

<210> SEQ ID NO 1
<211> LENGTH: 3082
<212> TYPE: DNA
<213> ORGANISM: Homo sapiens

<400> SEQUENCE: 1

```
ggcgtcgccg cgcggggaga aagaagccgc gcccagcccg gcgtcccgag cagcgcaggg        60
gaggatcccc gcgcagtgac ccgggagcca ccacagactc tgggaggctc ggcggctgga       120
gcagcaggca gctccccgca gctcccggcg cttccaggca gctctctgag ccgtgccaga       180
ggcccggccc gccattccca gccccgagcc atgatgaaga ctttgtccag cgggaactgc       240
acgctcagtg tgcccgccaa aaactcatac cgcatggtgg tgctgggtgc ctctcgggtg       300
ggcaagagct ccatcgtgtc tcgcttcctc aatggccgct ttgaggacca gtacacaccc       360
accatcgagg acttccaccg taaggtatac aacatccgcg gcgacatgta ccagctcgac       420
atcctggata cctctggcaa ccaccccttc cccgccatgc gcaggctgtc catcctcaca       480
ggggatgtct tcatcctggt gttcagcctg ataaccggga gtccttcga tgaggtcaag       540 cgccttcaga agcagatcct ggaggtcaag tcctgcctga agaacaagac caaggaggcg       600
gcggagctgc ccatggtcat ctgtggcaac aagaacgacc acggcgagct gtgccgccag       660
gtgcccacca ccgaggccga gctgctggtg tcgggcgacg agaactccgc ctacttcgag       720
gtgtcggcca agaagaacac caacgtggac gagatgttct acgtgctctt cagcatggcc       780
aagctgccac acgagatgag ccccgccctg catcgcaaga tctccgtgca gtacggtgac       840
gccttccacc ccaggccctt ctgcatgcgc cgcgtcaagg agatggacgc ctatggcatg       900
gtctcgccct tcgcccgccg ccccagcgtc aacagtgacc tcaagtacat caaggccaag       960
gtccttcggg aaggccaggc ccgtgagagg gacaagtgca ccatccagtg agcgagggat      1020
gctggggcgg ggcttggcca gtgccttcag ggaggtggcc ccagatgccc actgtgcgca      1080
tctccccacc gaggccccgg cagcagtctt gttcacagac cttaggcacc agactggagg      1140
cccccgggcg ctggcctccg cacattcgtc tgccttctca cagctttcct gagtccgctt      1200
gtccacagct ccttggtggt ttcatctcct ctgtgggagg acacatctct gcagcctcaa      1260
gagttaggca gagactcaag ttacaccttc ctctcctggg gttggaagaa atgttgatgc      1320
cagaggggtg aggattgctg cgtcatatgg agcctcctgg gacaagcctc aggatgaaaa      1380
```

-continued

```
ggacacagaa ggccagatga gaaaggtctc ctctctcctg gcataacacc cagcttggtt      1440
tgggtggcag ctgggagaac ttctctccca gccctgcaac tcttacgctc tggttcagct      1500
gcctctgcac ccctcccac ccccagcaca cacacaagtt ggcccccagc tgcgcctgac      1560
attgagccag tggactctgt gtctgaaggg ggcgtggcca cacctcctag accacgccca      1620
ccacttagac cacgcccacc tcctgaccgc gttcctcagc ctcctctcct aggtccctcc      1680
gcccgacagt tgtgctttgt tgtggttgca gctgttttcg tgtcatgtat agtagtagaa      1740
atggaaatca ttgtactgta aaagcctagt gactccctcc ttggccaggc cctcacccag      1800
ttcagatcca cggcctccac ccgggacgcc ttcctcctct gctcccaaac agggtttccg      1860
tggcctgttt gcagctagac attgacctcc gccattgagc tccacggttt acagacaatt      1920
gcacaagcgt ggggtgggca ggccaggact gcttttttt aatgctccca tttcacagag      1980
gataccaccg agactcggag gggacacgat gagcaccagg ccccacctt gtcccctagc      2040 aaattcaggg tacagctcca cctagaacca ggctgccctc tactgtgctc gttcctcaag      2100
catttattaa gcacctactg ggtgctgggt tcactgtgtc ctaggaaacc aagagggtcc      2160
ccagtcctgg cctctgcccg cccctgctgc cccaccacct tctgcacaca cagcggtggg      2220
gaggcgggga ggagcagctg ggacccagaa ctgagcctgg gagggatccg acagaaaagc      2280
tcagggcggg tcttctcctt gtgcccggga ttgggctatg ctgggtacca ccatgtactc      2340
aggcatggtg ggttttgaac ccataaacca aaggcccttg tcatcagctc ttaacaagta      2400
tattttgtat tttaatctct ctaaacatat tgaagtttta gggccctaag gaaccttagt      2460
gatcttctat tgggtctttc tgaggttcag agagggtaag taacttcctc caggtcacac      2520
agcaagtctg tgggtggcag aagcaagcta gcgctgggca ttcagtacat accacgatgt      2580
gctccctctc ttgatgcttg gcccctgggg ccttcagggc tttgggacat cttgtcctca      2640
accctctccc tagatcagtc tgtgagggtc cctgtagata ttgtgtacac catgcccatg      2700
tatatacaag tacacacaga tgtacacaca gatgtacaca tgctccagcc ccagctctgc      2760
atacctgcac ctgcacccca gccttggccc ctgcctgcgt ctgtgctcaa gcagcagct      2820 ccaaccctgc ctctgtcccc ttccccaccc actgcctgag ccttctgagc agaccaggta      2880
ccttggctgc accggtgtgt ggcccgctct cacccaggca cagccccgcc accatggatc      2940
tccgtgtaca ctatcaataa aagtgggttt gttacaaaaa aaaaaaaaaa aaaaaaaaaa      3000
aaaaaaaaaa aaaaaaaaaa aaaaaaaaaa aaaaaaaaaa aaaaaaaaaa aaaaaaaaaa      3060
aaaaaaaaaa aaaaaaaaaa aa                                              3082
```

<210> SEQ ID NO 2
<211> LENGTH: 266
<212> TYPE: PRT
<213> ORGANISM: Homo sapiens

<400> SEQUENCE: 2

```
Met Met Lys Thr Leu Ser Ser Gly Asn Cys Thr Leu Ser Val Pro Ala
 1               5                  10                  15

Lys Asn Ser Tyr Arg Met Val Val Leu Gly Ala Ser Arg Val Gly Lys
            20                  25                  30

Ser Ser Ile Val Ser Arg Phe Leu Asn Gly Arg Phe Glu Asp Gln Tyr
        35                  40                  45

Thr Pro Thr Ile Glu Asp Phe His Arg Lys Val Tyr Asn Ile Arg Gly
    50                  55                  60

Asp Met Tyr Gln Leu Asp Ile Leu Asp Thr Ser Gly Asn His Pro Phe
```

```
               65                  70                  75                  80
           Pro Ala Met Arg Arg Leu Ser Ile Leu Thr Gly Asp Val Phe Ile Leu
                           85                  90                  95
           Val Phe Ser Leu Asp Asn Arg Glu Ser Phe Asp Glu Val Lys Arg Leu
                          100                 105                 110
           Gln Lys Gln Ile Leu Glu Val Lys Ser Cys Leu Lys Asn Lys Thr Lys
                          115                 120                 125
           Glu Ala Ala Glu Leu Pro Met Val Ile Cys Gly Asn Lys Asn Asp His
                          130                 135                 140
           Gly Glu Leu Cys Arg Gln Val Pro Thr Thr Glu Ala Glu Leu Leu Val
           145                 150                 155                 160
           Ser Gly Asp Glu Asn Ser Ala Tyr Phe Glu Val Ser Ala Lys Lys Asn
                               165                 170                 175
           Thr Asn Val Asp Glu Met Phe Tyr Val Leu Phe Ser Met Ala Lys Leu
                           180                 185                 190
           Pro His Glu Met Ser Pro Ala Leu His Arg Lys Ile Ser Val Gln Tyr
                           195                 200                 205
           Gly Asp Ala Phe His Pro Arg Pro Phe Cys Met Arg Arg Val Lys Glu
                   210                 215                 220
           Met Asp Ala Tyr Gly Met Val Ser Pro Phe Ala Arg Arg Pro Ser Val
           225                 230                 235                 240
           Asn Ser Asp Leu Lys Tyr Ile Lys Ala Lys Val Leu Arg Glu Gly Gln
                               245                 250                 255
           Ala Arg Glu Arg Asp Lys Cys Thr Ile Gln
                           260                 265

<210> SEQ ID NO 3
<211> LENGTH: 11221
<212> TYPE: DNA
<213> ORGANISM: Homo sapiens

<400> SEQUENCE: 3
ctctctgact ctttgcctcc tctctgactc cctgcctcct ctctctgtct ccctgcctcc       60
tctgtctgac tccctgcctc ccctctctgt ctcactgcct cctctctctg actctctgcc      120
tcctctctct gactccctgc ctcctctctc tgattccctg cctctttgac cctctgcctc      180
ctctctttga ctccctgcct cctctctccg attctctgcg tctttgactc cctgcctcct      240
ctctctgact ccctgaagct cattcagtca ttgctatcaa ctcgtctgta ccaagctcta      300
ggctggaggc tgggcagggc aatgatggag acaaatactg tccctgggag cttctggccc      360
ctttcccatc ctgtttagac agaagtgacc gccagcagag tcaagctgtc tgcagaagga      420
cttggggagg gggctgtcat ggggtagggc ttctttcccc ccatctctgc tgaaggccca      480
ggctggctga gacagccccg gcagagactg agaagggctc cctgctgtgg tctggcagcc      540
ccctctccac cctcctctct tcatttcct gcctcccaca cgtatgccct gggcacctca      600
tcagggctgc cctaggggag ggccctcctt ggcacagccc ctgggccagt caggtggttg      660
aggctgagga gagaaggtcc cagagtgggg cttcaggcaa acccaaagac agagcccttt      720
gccatttgat gaatgcacag accctttatt gagcccctgc tctgttcatg gcatggcagt      780
tttgtgggat aaattcaaag acagctttag gtggagctgg gtggggat gtggggtct         840
taggcttgaa ctactaccca gcctcctttg ttaaccaagt agctagtcac gtagccttct      900
gagctcgggg cagaccacct gggatcaaac ctctcctctg ctggttactg gctgtgcaac      960
tgtaagcaag taatttaacc tctctgtgcc tcagtttcct catctgtaaa ttggagaata     1020
```

-continued

```
acaccacctg ctttctgggg ttatgaaggg agaaataggt taacatgtgt gcagcactta    1080
gaacactctg gcatatttta gctgcaaaat gaatgccagc tatgattatt tctatactta    1140
gtgcggggct tggcacactg catgggctca agtggcagca gttgtcgtcc ttgtggctcc    1200
aggcctgggg tccgccgtgt gctgagctgg cttattgtgc acgtcccttt gtgattcatt    1260
catcgaagtc acattagtag cttagaagtg accgtagtgg gagcatttac gccatggaaa    1320
ttggcaatag ggcttttaac aaaggtattt ttgagagccg gtttcctgca cagaggctgg    1380
tagttgggca gggtgagcag atccagatgt gtgccaggga ctcgcacgca ggcaatctct    1440
ccacctccag tggccatctc agaccttagc ttcatgatag ccaggaagcg atggtgttgg    1500
aaagcgcctt gggtcaatgg gcgaggcact caaggaaacc gacttggggc atcctggggt    1560
ggggaccgag tttgggcaca tacagccctt tgtgtgaatt taaaaacagt gccttttcct    1620
ctacacaaga tgccctttcg tctgggatac agccccacc tctgggatgc agcccccact    1680
tgcccaccca gccatgcgcc ttgtgcagta tccaacctgc acaacctgtg gcagcctgtg    1740
gaagaccgag gggattgata tttcagcagg cctgtgccca tttgcagttc aggggctgga    1800
aagctctcct ctggagaggg gagggattcc tgcaagggtg aggagatcag agaggccttc    1860
agagagcagg tggcacttga gccagaccct gaaacataag gggaagaggg tgttctgcag    1920
aggggtggca tgagcaaagg agtggaggct gatctcagca gagctcaaac tgacgagggt    1980
gactggggtc aggggttctg gggcggggat tctggtgggc gctaaggtag gaaaggaggg    2040
agggctgggc tgtgaagagc ctttgggtg agcctggtgg agcctgcggg tttgcttata    2100
caagagcttg gatccatgtc ggcctctttc atgaggtcaa gaggctccca tagaaagctc    2160
tgagtttgcc ccagaaccat aaccttggag atgggagggg aagcttgagc cagccatggg    2220
tcgttcccca ttccacatcc tctactccgg gcctctgggt ctcctggagg caagtaaaca    2280
cctagggcct gggaggcaaa aatatccggg caggtcatgg agcggaggga gcccgccaga    2340
tgcagagcac aggtctaaag gtgggtcctc ctgaggtggc tgcaggagca accccaggca    2400
ttgggcttgg agcatgcggt gtggacatag ccttcccttc ttcccaggag ggctgaatgg    2460
ccacagaacc accccctgcc ccaggcttaa gaaatgcatg ctagtgcctt ccccatgtct    2520
tatcctagaa tcacaggctc cgggaaagcc agatggatga accagggaaa gaacggattc    2580
tcaccataga taccattttt gagatttcac catgtgctga gcccttgca caactctat    2640 gaattgggct cattttgcag atgagaaaag tgacttctag agaggttaag ctactagccc    2700
aagatcagta gctagaggca aggcaaggat tcaaatccca ggagtccggt gcttgcataa    2760
atgaaaggat gaatgaacgg atattgagtg agtgagtgga tgaaggaagg agtaaaggag    2820
agggcatgaa tgaatgagag ggtagaactc caagacccct tagaacctcg tctgatgttc    2880
ccattttaca gacagaaaac tgagtcctag acagaggcct agaggaggcc aagaggtggt    2940
ggggccaggt cggggggggcc ctgatgcctg cttctctcgc tttgttgcag ccccgagcca    3000
tgatgaagac tttgtccagc gggaactgca cgctcagtgt gcccgccaaa aactcatacc    3060
gcatggtggt gctgggtgcc tctcgggtgg gcaagagctc catcgtgtct cgcttcctca    3120
atggccgctt tgaggaccag tacacaccca ccatcgagga cttccaccgt aaggtataca    3180
acatccgcgg cgacatgtac cagctcgaca tcctggatac ctctggcaac cacccttcc    3240 ccgccatgcg caggctgtcc atcctcacag gtgaggccca ctggtgcctg ggctggggcg    3300
gcagggccag ggcatggggtg cggagtgtgc tgggcacttg gcagtttgca tagacttgca    3360
```

-continued

| | |
|---|---|
| tagccatcgt ctgagacagg cgtcatccct gcacaatgag gctcagagag gttttgccat | 3420 |
| gtgctggaaa tagtgatgaa gtcgggggcc ccgattccat tctgttagac tccagatcga | 3480 |
| ttactcatgg ctgtcggggc cgccttccag atcaggagct gataccagca tgccccaggg | 3540 |
| atattccttt ctagggaaca gaatgatgcc ctggctgctg ctttccttct ccggaagatg | 3600 |
| acccaccaga gctccagggc ccaaggtcag tccacggggc tcaggtctcc cacaccccag | 3660 |
| gcctttgcca cctcctagag aggtaagggc aggacccagg cagtgatcac caaagggaag | 3720 |
| ggggcttggt catggtcata gtgatggtga tggcactagc tgacacttat cagaagctat | 3780 |
| gggcctggcc ctgttcttag agcttggcat gtagttttt ttgaaacaga gtctcgctct | 3840 |
| gtcacccagg ctggagtgca gtggcgcgat ctcggctcac tgcaacctct gcctcccggg | 3900 |
| ttcaagcgat tctcctgcct cagtccccca agtagctggg actacaggca cgtgccacca | 3960 |
| tgcccggcta atttttttgta tttttactag agacgggatt tcaccatgtt agccaggatg | 4020 |
| gtctcgatct cctgacctcg tgatctgcct acctcagcct cccaaagtgc tgagattaca | 4080 |
| ggcgtcagcc accgcggcca gccagcatgt agttatttaa ccctcacagt aaatagttat | 4140 |
| tcattccctt tttacaggtg gggaaactga agcccagaga ggttaagtaa ctcactccag | 4200 |
| tggtagcaca gctcgtaaag gcagtctgct tttgtgcttt cagacaaagc cataccacag | 4260 |
| cctctcagcc ctgctgggaa gggtgaggag ggacagggag gttgggggga agaaggggtga | 4320 |
| gtggagctg agggggctgtg cccttgttta cactgcatta gcatggtagc taagaggaca | 4380 |
| agcccgggac ccagcacctg ggtgtgagcc ctggttccgc tgcttcctgg ctttgtacct | 4440 |
| cgaggcaagg gattttatct ccttgtgtct cagcactctc atctgtaaga ctgcaccaca | 4500 |
| tcaacactca tcctaaaggg actgtgagac ttaaatgaat gaatatatgt aaggcgcttg | 4560 |
| gtgagcagat agtaaatgca caataaatcc ccaagtcttc tgttgagtca gcatttgcaa | 4620 |
| gtgggcctgc tacgggttac acgatcattt cccaagtcac gcccctgaag ttgctgagca | 4680 |
| gggataaggg aaggagtgag caggcaactc tctaggcatc attcagataa cccccccaact | 4740 |
| gaggtacttc tatacagaga aacccatgcc actcccagcc ctgctgccgc cttgaggcca | 4800 |
| agactgaggc tgcggggtgg cccctccttg agtgctttct cttccaggct ggcttttccg | 4860 |
| agcatctgac ccagacagca gtcaagttct ccgctccacc ccgagttttg gagaaggggc | 4920 |
| atgtagatag gagagccctg ggtcgacctg tgttcgaatc cttgctgggc ctcttggctt | 4980 |
| aaatgtgtga ccagaggcac atgcatcctg tctgagtctc agcctcccca gccacacagt | 5040 |
| gggcttaacc tcatacccccg cagggaggct gtgaggactg caagaaggct tgtggcggga | 5100 |
| gcttccagca cgtgacgggt attgcattgg tgtcagctcc cccagccttg gggaggggac | 5160 |
| tgggtacccg ctgcaatgaa taaggctaat gacagaggga aggagagggg agatgtagag | 5220 |
| aggaagcaca tgcatatttt cagcattaat tttcagtgac acaagtaata cccaaacaca | 5280 |
| ccctcctgca aacgctacag ataaagctaa tgccccttg acccatgtcc caatcccag | 5340 |
| gctcctgccc ctgccccgga ggtggccacc ctggcagtct ggcatggagc cttccgggcc | 5400 |
| tccgtgacta caccggcatt cgtatttgta tccccacaat ggagagtatt tttgtctgtc | 5460 |
| tcttttttat ggcgcatatc attctgagca cagctgtctg atgcttgttt ttttttcaca | 5520 |
| caccaacccg tgcctcattt tccaacctgg tggaacctca ttttttcaac ctcatttttcc | 5580 |
| tgctgctcag gaaattctga aagccattaa ttccactgcc agctcttctt ccagctgcca | 5640 |
| gacgggccga tctctgatgc ttggcatcgc agtctcgcat ttgaatatgt caaggccacg | 5700 |
| agtcctcagg ggccccggat tagcctaacg ggatggggtt tggcagccca agcaggaaga | 5760 |

-continued

```
gttgccaagc tgacgctgcc tcgcaagtgc ctttcagaag agcccacact gcagttccct    5820
ccatcacctc ccatccattc aggcttcctt ggttaacact gactgtgtgc caggccctgg    5880
ggagaccagg acgagtgggt gatggaaccc ttctctgtgc ccgagctgtt tggagcacac    5940
ctttgatctg acaccattc tgaatgtgcc atgtgccatt aaatgggggt aaatgatgtg    6000
ctctgggggt gcagaggaag gtggcagcca ttctgccaga agctggaact ggttgcttct    6060
cttctcaaga atttgggcca attgctgatt cctctgggcc tcagtttcct catctgtgag    6120
acagggatct tgtcacacca caaggctatc aagagtttga gcaaaagtgg ttggacgcag    6180
tggctcatgc ctgtaatccc agctctttgg gaggccgagg tgggcagatc tcttgaggtc    6240
aggagttcaa gaccagcctg gctaacacag tgaaacaccg tctctactaa aaatacaaa     6300 aaattagcca ggtgtggtga tgggcacctg taatcccagt tactcgggag gctgaggcag    6360
gagaatctct tgaacccagg aggtggaggt tgcagtgagc tgagatcttg ccattgcatt    6420
ccaggctggg caacaagagt gaaactctgt ctcagaaaat aaataaataa ataaataaaa    6480
aatagctagg catggtgaca ggcgcctgta atcccagctg ctccagaggc tgaggcagga    6540
gaatcgctta aacccaggag gtggaagttg cagtgagcca agatcacacc actgcactcc    6600
agcctgggcc acagagaaag actccatctc aaaaaaaaaa aaaaaaaaaa aaaaagttta    6660
agcaaaagtg aggaaggtgc ttattaaaag ctggaaatca ggatggaggt accagtccag    6720
acagcctccc caccacccca ccgtctccac agcagcccct gtttcagatt cacaagcctg    6780
ccttgagtga tgcagtgagt tatcctggag gcagtgtggg ccttggaggc cagcactcac    6840
tttttcatcc tatgatttat ttgagaagca gagagcacct accgggtgcc aggaacgagc    6900
taggtgagaa cagaatcagg tagaaatctc agcctagcca cacggaagct gtgtgatctt    6960
gggcaggctg cataccctt ctgagcctca gtttgctcac ctgtaatgca aggtaacaa     7020 aatcttgaca gaggcatagt gaggaatcaa gagaacaacg ggcctggagc atacacccag    7080
tgcttagccc ccagtaggcc ctcactctca tcattactga cacctgaggt cactgagcat    7140
gtgccactgt ccattcatta tcttgcataa ctcccaaaat catcctgcaa ggtaatattt    7200
catcttcatg aaacagacag agaaactgag gttacagagg tttcgtgatc tgcccaagtc    7260
tgctggcagc taagcggatg aggccagatg caaactaggc attgagcaag acaggcagga    7320
cccctgctct catagaaatg attttttatta ttatctgaac acagtccaca caagtgacct    7380
acccctctcc agccctgcaa agaaatgtga agtgagttaa ctgtatttga accaagtggt    7440
ccacgtgtta gctatgcgac tgtgaacagg ggcttcaacc ccctcagcct cagtttcctg    7500
tcctggaaaa taatcgcagg gagaataatc gcagctaccc cgaagagtcg ctgtgtaggt    7560
taaagcagtt atgccgcata actgcttcag ggcacctgtg actcccagct cttagggctg    7620
atgttctgtg gccagaggag ggcagggggtt gcagctggcc ggtgaactca ctacctgggc    7680
tctctccctg caggggatgt cttcatcctg gtgttcagcc tggataaccg ggagtccttc    7740
gatgaggtca agcgcttca gaagcagatc ctggaggtca gtcctgcct gaagaacaag    7800 accaaggagg cggcggagct gcccatggtc atctgtggca acaagaacga ccacggcgag    7860
ctgtgccgcc aggtgcccac caccgaggcc gagctgctgg tgtcgggcga cgagaactgc    7920
gcctacttcg aggtgtcggc caagaagaac accaacgtgg acgagatgtt ctacgtgctc    7980
ttcagcatgg ccaagctgcc acacgagatg agcccgccc tgcatcgcaa gatctccgtg    8040
cagtacggtg acgccttcca cccccaggccc ttctgcatgc gccgcgtcaa ggagatggac    8100
```

```
gcctatggca tggtctcgcc cttcgcccgc cgccccagcg tcaacagtga cctcaagtac   8160
atcaaggcca aggtccttcg ggaaggccag gcccgtgaga gggacaagtg caccatccag   8220
tgagcgaggg atgctgggc ggggcttggc cagtgccttc agggaggtgg ccccagatgc    8280
ccactgtgcg catctcccca ccgaggcccc ggcagcagtc ttgttcacag accttaggca   8340
ccagactgga ggcccccggg cgctggcctc cgcacattcg tctgccttct cacagctttc   8400
ctgagtccgc ttgtccacag ctccttggtg gtttcatctc ctctgtggga ggacacatct   8460
ctgcagcctc aagagttagg cagagactca agttacacct tcctctcctg gggttggaag   8520
aaatgttgat gccagagggg tgaggattgc tgcgtcatat ggagcctcct gggacaagcc   8580
tcaggatgaa aaggacacag aaggccagat gagaaaggtc tcctctctcc tggcataaca   8640
cccagcttgg tttgggtggc agctgggaga acttctctcc cagccctgca actcttacgc   8700
tctggttcag ctgcctctgc accccctccc accccagca cacacacaag ttggccccca    8760
gctgcgcctg acattgagcc agtggactct gtgtctgaag gggcgtggc cacacctcct    8820
agaccacgcc caccacttag accacgccca cctcctgacc gcgttcctca gcctcctctc   8880
ctaggtccct ccgcccgaca gttgtgcttt gttgtggttg cagctgtttt cgtgtcatgt   8940
atagtagtag aaatggaaat cattgtactg taaaagccta gtgactccct ccttggccag   9000
gccctcaccc agttcagatc cacggcctcc acccgggacg ccttcctcct ctgctcccaa   9060
acagggtttc cgtggcctgt ttgcagctag acattgacct ccgccattga gctccacggt   9120
ttacagacaa ttgcacaagc gtggggtggg caggccagga ctgctttttt ttaatgctcc   9180
catttcacag aggataccac cgagactcgg aggggacacg atgagcacca ggccccacct   9240
ttgtccccta gcaaattcag ggtacagctc cacctagaac caggctgccc tctactgtgc   9300
tcgttcctca agcatttatt aagcacctac tgggtgctgg gttcactgtg tcctaggaaa   9360
ccaagagggt ccccagtcct ggcctctgcc cgccccctgct gccccaccac cttctgcaca   9420
cacagcggtg gggaggcggg gaggagcagc tgggacccag aactgagcct gggagggatc   9480
cgacagaaaa gctcagggcg ggtcttctcc ttgtgcccgg gattgggcta tgctgggtac   9540
caccatgtac tcaggcatgg tgggttttga acccataaac caaaggccct tgtcatcagc   9600
tcttaacaag tatattttgt attttaatct ctctaaacat attgaagttt tagggcccta   9660
aggaacctta gtgatcttct attgggtctt tctgaggttc agagagggta agtaacttcc   9720
tccaggtcac acagcaagtc tgtgggtggc agaagcaagc tagcgctggg cattcagtac   9780
ataccacgat gtgctccctc tcttgatgct tggcccctgg ggccttcagg gctttgggac   9840
atcttgtcct caaccctctc cctagatcag tctgtgaggg tccctgtaga tattgtgtac   9900
accatgccca tgtatataca agtacacaca gatgtacaca cagatgtaca catgctccag   9960
ccccagctct gcatacctgc acctgcaccc cagccttggc ccctgcctgc gtctgtgctc  10020
aaagcagcag ctccaaccct gcctctgtcc ccttccccac ccactgcctg agccttctga  10080
gcagaccagg taccttggct gcaccggtgt gtggcccgct ctcacccagg cacagccccg  10140
ccaccatgga tctccgtgta cactatcaat aaaagtgggt tgttacaaa gccgtgtcct   10200
tgcccatgtg tattttttgt atttccaaga ggaggtgtgc ccctttccag accaaagctg  10260
gcctttccct cccaaaatgc acctgccgtg taccctggcc ctgagggtca gcactgagtc  10320
caccttcaag tgtaagtgtg gggagagggg gataagtccc ccagatggaa ggtgatgccc  10380
tccttcagcc tggccctcct gggtcctccg ggtgtgtgta ccgaggtgtc tgtgtccaca  10440
aagaagggc ccccgtggac cattagctcc aggaggatct ccgtgtctga gttctttgtg   10500
```

```
attcctgtac agcagcaatt tcacccgcag gggacagttg gcaatctctg gaaacctttt    10560
ccaagcctgg ggctggggct gctactctca tctggtgggt ggaggccagg gacaccattc    10620
agtatcctcc aacgcacagg atgcccctcc acccccaccc cactgagaat tatctggcct    10680
caaatgccaa gcgtgggcag ccttacttag actcacccca ggggctggga cacgccccca    10740
cctgcgtgtg atggatttgt tggaccacat tctggacgga acccacagca taagcactcc    10800
tgtgaagtga gacaggatgt gggtgaggat ggaaagtgga ggctgaggga aaggtctgg     10860
gccctgacca acacggaatg tgcccctgg gactgagagg cttccctggg cagagggaaa     10920
ggaggaagtc agtgaggtaa atactccct gtgtgtttta cccagcgagt ctcacgccat     10980
cctatcaccc agccccgagg aagcccact catgttcacc ccatctgagc atttaggctc     11040
agagagctca atatcttgtc caagatggca cagctggtga agtggcagat cagagattca    11100
acaccagagg ctgtctgatt tccgtctggc tgaagaaaga ttttgcatca gggaggtgga    11160
aaccatctgt gcttttgatc agcaaatgcc accagcagga tcagggagcc aggccataaa    11220
g                                                                    11221
```

<210> SEQ ID NO 4
<211> LENGTH: 266
<212> TYPE: PRT
<213> ORGANISM: Homo sapiens

<400> SEQUENCE: 4

```
Met Met Lys Thr Leu Ser Ser Gly Asn Cys Thr Leu Ser Val Pro Ala
 1               5                  10                  15

Lys Asn Ser Tyr Arg Met Val Val Leu Gly Ala Ser Arg Val Gly Lys
            20                  25                  30

Ser Ser Ile Val Ser Arg Phe Leu Asn Gly Arg Phe Glu Asp Gln Tyr
        35                  40                  45

Thr Pro Thr Ile Glu Asp Phe His Arg Lys Val Tyr Asn Ile Arg Gly
    50                  55                  60

Asp Met Tyr Gln Leu Asp Ile Leu Asp Thr Ser Gly Asn His Pro Phe
65                  70                  75                  80

Pro Ala Met Arg Arg Leu Ser Ile Leu Thr Gly Asp Val Phe Ile Leu
                85                  90                  95

Val Phe Ser Leu Asp Asn Arg Glu Ser Phe Asp Glu Val Lys Arg Leu
            100                 105                 110

Gln Lys Gln Ile Leu Glu Val Lys Ser Cys Leu Lys Asn Lys Thr Lys
        115                 120                 125

Glu Ala Ala Glu Leu Pro Met Val Ile Cys Gly Asn Lys Asn Asp His
    130                 135                 140

Gly Glu Leu Cys Arg Gln Val Pro Thr Thr Glu Ala Glu Leu Leu Val
145                 150                 155                 160

Ser Gly Asp Glu Asn Cys Ala Tyr Phe Glu Val Ser Ala Lys Lys Asn
                165                 170                 175

Thr Asn Val Asp Glu Met Phe Tyr Val Leu Phe Ser Met Ala Lys Leu
            180                 185                 190

Pro His Glu Met Ser Pro Ala Leu His Arg Lys Ile Ser Val Gln Tyr
        195                 200                 205

Gly Asp Ala Phe His Pro Arg Pro Phe Cys Met Arg Arg Val Lys Glu
    210                 215                 220

Met Asp Ala Tyr Gly Met Val Ser Pro Phe Ala Arg Arg Pro Ser Val
225                 230                 235                 240
```

-continued

Asn Ser Asp Leu Lys Tyr Ile Lys Ala Lys Val Leu Arg Glu Gly Gln
                245                 250                 255

Ala Arg Glu Arg Asp Lys Cys Thr Ile Gln
            260                 265

<210> SEQ ID NO 5
<211> LENGTH: 266
<212> TYPE: PRT
<213> ORGANISM: Rattus norvegicus

<400> SEQUENCE: 5

Met Met Lys Thr Leu Ser Ser Gly Asn Cys Thr Leu Asn Val Pro Ala
 1               5                  10                  15

Lys Asn Ser Tyr Arg Met Val Val Leu Gly Ala Ser Arg Val Gly Lys
                20                  25                  30

Ser Ser Ile Val Ser Arg Phe Leu Asn Gly Arg Phe Glu Asp Gln Tyr
            35                  40                  45

Thr Pro Thr Ile Glu Asp Phe His Arg Lys Val Tyr Asn Ile His Gly
    50                  55                  60

Asp Met Tyr Gln Leu Asp Ile Leu Asp Thr Ser Gly Asn His Pro Phe
65                  70                  75                  80

Pro Ala Met Arg Arg Leu Ser Ile Leu Thr Gly Asp Val Phe Ile Leu
                85                  90                  95

Val Phe Ser Leu Asp Ser Arg Glu Ser Phe Asp Glu Val Lys Arg Leu
                100                 105                 110

Gln Lys Gln Ile Leu Glu Val Lys Ser Cys Leu Lys Asn Lys Thr Lys
            115                 120                 125

Glu Ala Ala Glu Leu Pro Met Val Ile Cys Gly Asn Lys Asn Asp His
            130                 135                 140

Ser Glu Leu Cys Arg Gln Val Pro Ala Met Glu Ala Glu Leu Leu Val
145                 150                 155                 160

Ser Gly Asp Glu Asn Cys Ala Tyr Phe Glu Val Ser Ala Lys Lys Asn
                165                 170                 175

Thr Asn Val Asn Glu Met Phe Tyr Val Leu Phe Ser Met Ala Lys Leu
                180                 185                 190

Pro His Glu Met Ser Pro Ala Leu His His Lys Ile Ser Val Gln Tyr
            195                 200                 205

Gly Asp Ala Phe His Pro Arg Pro Phe Cys Met Arg Arg Thr Lys Val
    210                 215                 220

Ala Gly Ala Tyr Gly Met Val Ser Pro Phe Ala Arg Arg Pro Ser Val
225                 230                 235                 240

Asn Ser Asp Leu Lys Tyr Ile Lys Ala Lys Val Leu Arg Glu Gly Gln
                245                 250                 255

Ala Arg Glu Arg Asp Lys Cys Ser Ile Gln
            260                 265

<210> SEQ ID NO 6
<211> LENGTH: 7
<212> TYPE: PRT
<213> ORGANISM: Homo sapiens
<220> FEATURE:
<221> NAME/KEY: VARIANT
<222> LOCATION: (1)...(7)
<223> OTHER INFORMATION: Xaa = Any Amino Acid

<400> SEQUENCE: 6

Gly Xaa Xaa Xaa Xaa Gly Lys

-continued

```
<210> SEQ ID NO 7
<211> LENGTH: 5
<212> TYPE: PRT
<213> ORGANISM: Homo sapiens

<400> SEQUENCE: 7

Asp Thr Ala Gly Gln
 1               5

<210> SEQ ID NO 8
<211> LENGTH: 4
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid

<400> SEQUENCE: 8

Asn Lys Xaa Asp
 1

<210> SEQ ID NO 9
<211> LENGTH: 5
<212> TYPE: PRT
<213> ORGANISM: Homo sapiens
<220> FEATURE:
<221> NAME/KEY: VARIANT
<222> LOCATION: (1)...(5)
<223> OTHER INFORMATION: Xaa = Any Amino Acid

<400> SEQUENCE: 9

Glu Xaa Ser Ala Xaa
 1               5
```

ISOLATED HUMAN RAS-LIKE PROTEINS, NUCLEIC ACID MOLECULES ENCODING THESE HUMAN RAS-LIKE PROTEINS, AND USES THEREOF

FIELD OF THE INVENTION

The present invention is in the field of Ras-like proteins that are related to the dexamethasone-induced Ras subfamily, recombinant DNA molecules and protein production. The present invention specifically provides novel Ras-like protein polypeptides and proteins and nucleic acid molecules encoding such peptide and protein molecules, all of which are useful in the development of human therapeutics and diagnostic compositions and methods.

BACKGROUND OF THE INVENTION

Ras-like proteins, particularly members of the dexamethasone-induced Ras subfamilies, are a major target for drug action and development. Accordingly, it is valuable to the field of pharmaceutical development to identify and characterize previously unknown members of these subfamily of Ras-like proteins. The present invention advances the state of the art by providing a previously unidentified human Ras-like proteins that have homology to members of the dexamethasone-induced Ras subfamilies.

Ras Protein

Ras proteins are small regulatory GTP-binding proteins, or small G proteins, which belong to the Ras protein superfamily. They are monomeric GTPases, but their GTPase activity is very slow (less than one GTP molecule per minute).

Ras proteins are key relays in the signal transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF). . . ), insulin, an interleukin (IL), granulocyte colony-stimulating factor (G-CSF), granulocyte/macrophage colony-stimulating factor (GM-CSF). . . .

Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Ras proteins alternate between an inactive form bound to GDP and an active form bound to GTP. Their activation results from reactions induced by a guanine nucleotide-exchange factor (GEF). Their inactivation results from reactions catalyzed by a GTPase-activating protein (GAP).

When a Ras protein is activated by a GEF such as a Sos protein, the N-terminal region of a serine/threonine kinase, called "Raf protein", can bind to Ras protein. The C-terminal region of the activated Raf thus formed binds to another protein, MEK, and phosphorylates it on both specific tyrosine and serine residues. Active MEK phosphorylates and activates, in turn, a MAP kinase (ERK1 or ERK2), which is also a serine/threonine kinase. This phosphorylation occurs on both specific tyrosine and threonine residues of MAP kinase.

MAP kinase phosphorylates many different proteins, especially nuclear transcription factors (TFs) which regulate expression of many genes during cell proliferation and differentiation.

Recent researches suggest that, in mammalians, phosphatidyl inositol 3'-kinase (PI3-kinase) might be a target of Ras protein, instead of Raf protein. In certain mutations, the translation of ras genes may produce oncogenic Ras proteins.

Ras-like Protein

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal transducing proteins are members of the Ras superfamily.

The Ras superfamily is a class of low molecular weight (LMW) GTP-binding proteins which consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization which is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the R superfamily share conserved structural features. Four conserved sequence regions (motif I–IV) have been studied in the LMW GTP-binding proteins. Motif I is the most variable but has the conserved sequence, GXXXXGK (SEQ ID NO:6). The lysine residue is essential in interacting with the .beta.- and .gamma.-phosphates of GTP. Motif II, III, and IV contain highly conserved sequences of DTAGQ (SEQ ID NO:7) NKXD SEQ ID NO:8), and EXSAX (SEQ ID NO:9), respectively. Specifically, Motif II regulates the binding of gamma-phosphate of GTP; Motif III regulates the binding of GTP; an Motif IV regulates the guanine base of GTP. Most of the membrane-bound LMW GTP-binding proteins generally require a carboxy terminal isoprenyl group for membrane association and biological activity. The isoprenyl group is added posttranslationally through recognition of a terminal cysteine residue alone or a terminal cysteine-aliphatic amino acid-aliphatic amino acid-any amino acid (CAAX) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARL184 is active in both the cytosol and the Golgi apparatus and is closely associated with acetylcholine release, suggesting that ARL184 is a potential regulatory protein associated with $Ca^{2+}$-dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. et al. (1993) Philos. Trans. R. Soc. Lond. (Biol.) 340:267–271). All Rho proteins have a CAAX motif which binds a prenyl group and either a palmitoylation site or a basic amino acid-rich region, suggesting their role in membrane-associated functions. In particular, RhoD is a protein which functions in early endosome motility and distribution by inducing rearrangement of actin cytoskeleton and cell surface (Murphy, C. et al. (1996) Nature 384:427–432). During cell adhesion, the Rho proteins are essential for triggering focal complex assembly and integrin-dependent signal transduction (Hotchin, N. A. and Hall, A. (1995) J. Cell Biol. 131:1857–1865).

The Ras subfamily proteins already indicated supra are essential in transducing signals from receptor tyrosine kinases (RTKs) to a series of serine/threonine kinases which control cell growth and differentiation. Mutant Ras proteins, which bind but cannot hydrolyze GTP, are permanently activated and cause continuous cell proliferation or cancer. TC21, a Ras-like protein, is found to be highly expressed in a human teratocarcinoma cell line (Drivas, G. T. et al. (1990) Mol. Cell. Biol. 10: 1793–1798). Rin and Rit are characterized as membrane-binding, Ras-like proteins without the lipid-binding CAAX motif and carboxy terminal cysteine (Lee, C.-H. J. et al. (1996) J. Neurosci. 16: 6784–6794). Further, Rin is shown to localize in neurons and have calcium-dependant calmodulin-binding activity.

The discovery of a new human Ras-like proteins and the polynucleotides which encode them satisfies a need in the art by providing new compositions which are useful in the diagnosis, prevention, and treatment of inflammation and disorders associated with cell proliferation and apoptosis.
Dexamethasone-Induced Ras The novel human protein, and encoding gene, provided by the present invention is related to the family of dexamethasone-induced Ras ("DexRas") proteins, particularly mouse DexRas1, human tumor endothelial marker 2, and rat Rhes protein.

Specifically, the public human tumor endothelial marker 2 protein (Genbank entry GI:10047088) is predicted to have 12 additional amino acid residues on the N-terminal end of the protein compared with the protein provided by the present invention (illustrated in FIG. 2). Furthermore, the N-terminal end of the rat Dexras1 protein (Genbank entry GI:5059122) matches the N-terminal end of the human protein of the present invention, thus suggesting that the art-known protein prediction for the human tumor endothelial marker 2/DexRas1 protein is a false protein prediction.

DexRas proteins may play important roles in tumor angiogenesis, wound healing, and corpus luteum formation (St Croix et al., Science 2000 Aug. 18;289(5482) :1197–202). They may play an important role in angiogenesis in a wide variety of tumors, particularly colorectal tumors and numerous tumors involving the endothelium. Therefore, novel human DexRas proteins/genes may be medically and commercially valuable for cancer diagnosis/treatment and for developing anti-angiogenic and anti-cancer therapeutics.

SUMMARY OF THE INVENTION

The present invention is based in part on the identification of amino acid sequences of human Ras-like protein polypeptides and proteins that are related to the dexamethasone-induced Ras-like protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate Ras-like protein activity in cells and tissues that express the Ras-like protein. Experimental data as provided in FIG. 1 indicates expression in humans in placenta choriocarcinomas, uterus endometrium adenocarcinomas, skin melanotic melanomas, and fetal brain.

DESCRIPTION OF THE FIGURE SHEETS

FIG. 1 provides the nucleotide sequence of a cDNA molecule that encodes the Ras-like protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in placenta choriocarcinomas, uterus endometrium adenocarcinomas, skin melanotic melanomas, and fetal brain.

FIG. 1 also provides analysis of the 5' UTR region of the gene encoding the Ras-like protein of the present invention. Computational analysis of the 5' UTR indicates the presence of two non-coding exons and a third exon that is partially non-coding and partially coding (protein coding region begins at nucleotide 211). Computational analysis of the 5' UTR also indicates that there are no upstream in-frame stop codons.

FIG. 2 provides the predicted amino acid sequence of the Ras-like protein of the present invention. (SEQ ID NO:2) In addition structure and functional information such as protein family, function, and modification sites is provided where available, allowing one to readily determine specific uses of inventions based on this molecular sequence. FIG. 2 also provides the complete amino acid sequence of Genbank entry gi|10047088, the closest art-known protein, illustrating the 12 additional N-terminal amino acid residues (underlined residues) present in the art-known protein that are not found in the protein of the present invention.

FIG. 3 provides genomic sequences that span the gene encoding the Ras-like protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, the following SNPs have been identified: C3951T, C4127T, G4157A, C4513T, C6894A, G8409C, T8437G, T8579C, A10292G, and A10792G.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a Ras-like protein or part of a Ras-like protein and are related to the dexamethasone-induced Ras subfamily. Utilizing these sequences, additional genomic sequences were assembled and transcript and/or cDNA sequences were isolated and characterized. Based on this analysis, the present invention provides amino acid sequences of human Ras-like protein polypeptides that are related to the dexamethasone-induced Ras subfamily, nucleic acid sequences in the form of transcript sequences, cDNA sequences and/or genomic sequences that encode these Ras-like protein polypeptide, nucleic acid variation (allelic information), tissue distribution of expression, and information about the closest art known protein/peptide/domain that has structural or sequence homology to the Ras-like protein of the present invention.

In addition to being previously unknown, the peptides that are provided in the present invention are selected based on their ability to be used for the development of commercially important products and services. Specifically, the present peptides are selected based on homology and/or structural relatedness to known Ras-like proteins of the dexamethasone-induced Ras subfamily and the expression pattern observed. Experimental data as provided in FIG. 1 indicates expression in humans in placenta choriocarcinomas, uterus endometrium adenocarcinomas, skin melanotic melanomas, and fetal brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known dexamethasone-induced Ras family or subfamily of Ras-like proteins.

Specific Embodiments

Peptide Molecules

The present invention provides nucleic acid sequences that encode protein molecules that have been identified as being members of the Ras-like protein family and are related to the dexamethasone-induced Ras subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the Ras-like proteins or peptides of the present invention, Ras-like proteins or peptides, or peptides/proteins of the present invention.

The present invention provides isolated peptide and protein molecules that consist of, consist essentially of, or comprise the amino acid sequences of the Ras-like protein polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the Ras-like protein polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated Ras-like protein polypeptide can be purified from cells that naturally express it, purified from cells that have been altered to express it (recombinant), or synthesized using known protein synthesis methods. Experimental data as provided in FIG. 1 indicates expression in humans in placenta choriocarcinomas, uterus endometrium adenocarcinomas, skin melanotic melanomas, and fetal brain. For example, a nucleic acid molecule encoding the Ras-like protein polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1

(SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the Ras-like protein polypeptide of the present invention are the naturally occurring mature proteins. A brief description of how various types of these proteins can be made/isolated is provided below.

The Ras-like protein polypeptides of the present invention can be attached to heterologous sequences to form chimeric or fusion proteins. Such chimeric and fusion proteins comprise a Ras-like protein polypeptide operatively linked to a heterologous protein having an amino acid sequence not substantially homologous to the Ras-like protein polypeptide. "Operatively linked" indicates that the Ras-like protein polypeptide and the heterologous protein are fused in-frame. The heterologous protein can be fused to the N-terminus or C-terminus of the Ras-like protein polypeptide.

In some uses, the fusion protein does not affect the activity of the Ras-like protein polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Ras-like protein polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A Ras-like protein polypeptide-encoding nucleic acid can be cloned into such an expression vector such that the fusion moiety is linked in-frame to the Ras-like protein polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the Ras-like protein polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10(1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When tilizing BLAST and gapped BLAST programs, the default parameters of the respectiv programs (e.g., XBLAST and NBLAST) can be used.

Full-length pre-processed forms, as well as mature processed forms, of proteins that comprise one of the peptides of the present invention can readily be identified as having complete sequence identity to one of the Ras-like protein polypeptides of the present invention as well as being encoded by the same genetic locus as the Ras-like protein polypeptide provided herein. The gene encoding the novel Ras-like protein of the present invention is located on a genome component that has been mapped to human chromosome 22 (as indicated in FIG. 3), which is supported by multiple lines of evidence, such as STS and BAC map data.

Allelic variants of a Ras-like protein polypeptide can readily be identified as being a human protein having a high degree (significant) of sequence homology/identity to at least a portion of the Ras-like protein polypeptide as well as being encoded by the same genetic locus as the Ras-like protein polypeptide provided herein. Genetic locus can readily be determined based on the genomic information provided in FIG. 3, such as the genomic sequence mapped to the reference human. The gene encoding the novel Ras-like protein of the present invention is located on a genome component that has been mapped to human chromosome 22 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a Ras-like protein polypeptide encoding nucleic acid molecule under stringent conditions as more fully described below.

FIG. 3 provides information on SNPs that have been found in the gene encoding the Ras-like protein of the present invention. The following variations were identified: C3951T, C4127T, G4157A, C4513T, C6894A, G8409C, T8437G, T8579C, A10292G, and A10792G. These SNPs may affect control/regulatory elements.

Paralogs of a Ras-like protein polypeptide can readily be identified as having some degree of significant sequence homology/identity to at least a portion of the Ras-like protein polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a Ras-like protein polypeptide encoding nucleic acid molecule under moderate to stringent conditions as more fully described below.

Orthologs of a Ras-like protein polypeptide can readily be identified as having some degree of significant sequence homology/identity to at least a portion of the Ras-like protein polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a Ras-like protein polypeptide encoding nucleic acid molecule under moderate to stringent conditions, as more fully described below, depending on the degree of relatedness of the two organisms yielding the proteins.

Non-naturally occurring variants of the Ras-like protein polypeptides of the present invention can readily be generated using recombinant techniques. Such variants include, but are not limited to deletions, additions and substitutions in the amino acid sequence of the Ras-like protein polypeptide. For example, one class of substitutions is conserved amino acid substitutions. Such substitutions are those that substitute a given amino acid in a Ras-like protein polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., *Science* 247:1306–1310 (1990).

Variant Ras-like protein polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., *J. Mol. Biol.* 224:899–904 (1992); de Vos et al. *Science* 255:306–312 (1992)).

The present invention further provides fragments of the Ras-like protein polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a Ras-like protein polypeptide. Such fragments can be chosen based on the ability to retain one or more of the biological activities of the Ras-like protein polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the Ras-like protein polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Ras-like protein polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W.H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the Ras-like protein polypeptides of the present invention also encompass derivatives or analogs in which a substituted amino acid residue is not one encoded by the genetic code, in which a substituent group is included, in which the mature Ras-like protein polypeptide is fused with another compound, such as a compound to increase the half-life of the Ras-like protein polypeptide (for example, polyethylene glycol), or in which the additional amino acids are fused to the mature Ras-like protein polypeptide, such as a leader or secretory sequence or a sequence for purification of the mature Ras-like protein polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, Ras-like proteins isolated from humans and their human/mammalian orthologs serve as targets for identifying agents for use in mammalian therapeutic applications, e.g. a human drug, particularly in modulating a biological or pathological response in a cell or tissue that expresses the Ras-like protein. Experimental data as provided in FIG. 1 indicates that the Ras-like proteins of the present invention are expressed in humans in placenta choriocarcinomas, uterus endometrium adenocarcinomas, and skin melanotic melanomas, as indicated by virtual northern blot analysis. In addition, PCR-based tissue screening panels indicate expression in fetal brain. A large percentage of pharmaceutical agents are being developed that modulate the activity of Ras-like proteins, particularly members of the dexamethasone-induced Ras subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in placenta choriocarcinomas, uterus endometrium adenocarcinomas, skin melanotic melanomas, and fetal brain. Such uses can readily be determined using the information provided herein, that which is known in the art, and routine experimentation.

The proteins of the present invention (including variants and fragments that may have been disclosed prior to the present invention) are useful for biological assays related to Ras-like proteins that are related to members of the dexamethasone-induced Ras subfamily. Such assays involve any of the known Ras-like protein functions or activities or properties useful for diagnosis and treatment of Ras-like protein-related conditions that are specific for the subfamily of Ras-like proteins that the one of the present invention belongs to, particularly in cells and tissues that express the Ras-like protein. Experimental data as provided in FIG. 1 indicates that the Ras-like proteins of the present invention are expressed in humans in placenta choriocarcinomas, uterus endometrium adenocarcinomas, and skin melanotic melanomas, as indicated by virtual northern blot analysis. In addition, PCR-based tissue screening panels indicate expression in fetal brain.

The proteins of the present invention are also useful in drug screening assays, in cell-based or cell-free systems. Cell-based systems can be native, i.e., cells that normally express the Ras-like protein, as a biopsy or expanded in cell culture. Experimental data as provided in FIG. 1 indicates expression in humans in placenta choriocarcinomas, uterus endometrium adenocarcinomas, skin melanotic melanomas, and fetal brain. In an alternate embodiment, cell-based assays involve recombinant host cells expressing the Ras-like protein.

The polypeptides can be used to identify compounds that modulate Ras-like protein activity. Both the Ras-like protein of the present invention and appropriate variants and fragments can be used in high-throughput screens to assay candidate compounds for the ability to bind to the Ras-like protein. These compounds can be further screened against a functional Ras-like protein to determine the effect of the compound on the Ras-like protein activity. Further, these compounds can be tested in animal or invertebrate systems to determine activity/effectiveness. Compounds can be identified that activate (agonist) or inactivate (antagonist) the Ras-like protein to a desired degree.

Therefore, in one embodiment, dexamethasone-induced Ras or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising dexamethasone-induced Ras may be administered to a subject to prevent or treat a disorder associated with increased apoptosis including, but not limited to, those listed above.

In still another embodiment, an agonist which is specific for dexamethasone-induced Ras may be administered to prevent or treat a disorder associated with increased apoptosis including, but not limited to, those listed above.

In a further embodiment, a vector capable of expressing dexamethasone-induced Ras, or a fragment or a derivative thereof, may be used to prevent or treat a disorder associated with increased apoptosis including, but not limited to, those listed above.

In cancer, where dexamethasone-induced Ras promotes cell proliferation, it is desirable to decrease its activity. Therefore, in one embodiment, an antagonist of dexamethasone-induced Ras may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for dexamethasone-induced Ras may be used directly as an antagonist, or indirectly as a targeting or delivery mechanism for bringing a pharmaceutical agent to cells or tissue which express dexamethasone-induced Ras.

In another embodiment, a vector expressing the complement of the polynucleotide encoding dexamethasone-induced Ras may be administered to a subject to prevent or treat a cancer including, but not limited to, the types of cancer listed above.

In inflammation, where dexamethasone-induced Ras promotes cell proliferation, it is desirable to decrease its activity. Therefore, in one embodiment, an antagonist of dexamethasone-induced Ras may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for dexamethasone-induced Ras may be used directly as an antagonist, or indirectly as a targeting or delivery mechanism for bringing a pharmaceutical agent to cells or tissue which express dexamethasone-induced Ras.

Further, the Ras-like protein polypeptides can be used to screen a compound for the ability to stimulate or inhibit interaction between the Ras-like protein and a molecule that normally interacts with the Ras-like protein, e.g. a ligand or a component of the signal pathway that the Ras-like protein normally interacts. Such assays typically include the steps of combining the Ras-like protein with a candidate compound under conditions that allow the Ras-like protein, or fragment, to interact with the target molecule, and to detect the formation of a complex between the protein and the target or to detect the biochemical consequence of the interaction with the Ras-like protein and the target, such as any of the associated effects of signal transduction.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries). (Hodgson, Bio/technology, 1992, Sep. 10(9);973–80).

One candidate compound is a soluble fragment of the Ras-like protein that competes for ligand binding. Other candidate compounds include mutant Ras-like proteins or appropriate fragments containing mutations that affect Ras-like protein function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) Ras-like protein activity. The assays typically involve an assay of events in the Ras-like protein mediated signal transduction pathway that indicate Ras-like protein activity. Thus, the phosphorylation of a protein/ligand target, the expression of genes that are up- or down-regulated in response to the Ras-like protein dependent signal cascade can be assayed. In one embodiment, the regulatory region of such genes can be operably linked to a marker that is easily detectable, such as luciferase. Alternatively, phosphorylation of the Ras-like protein, or a Ras-like protein target, could also be measured.

Any of the biological or biochemical functions mediated by the Ras-like protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric Ras-like proteins in which any of the protein's domains, or parts thereof, can be replaced by heterologous domains or subregions. Accordingly, a different set of signal transduction components is available as an end-point assay for activation. This allows for assays to be performed in other than the specific host cell from which the Ras-like protein is derived.

The Ras-like protein polypeptide of the present invention is also useful in competition binding assays in methods designed to discover compounds that interact with the Ras-like protein. Thus, a compound is exposed to a Ras-like protein polypeptide under conditions that allow the compound to bind or to otherwise interact with the polypeptide. Soluble Ras-like protein polypeptide is also added to the mixture. If the test compound interacts with the soluble Ras-like protein polypeptide, it decreases the amount of complex formed or activity from the Ras-like protein target. This type of assay is particularly useful in cases in which compounds are sought that interact with specific regions of the Ras-like protein. Thus, the soluble polypeptide that competes with the target Ras-like protein region is designed to contain peptide sequences corresponding to the region of interest.

To perform cell free drug screening assays, it is sometimes desirable to immobilize either the Ras-like protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Ras-like protein-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a Ras-like protein-binding protein and a candidate compound are incubated in the Ras-like protein-presenting wells and the amount of complex trapped in the well can be quantitated. Methods for detecting such complexes, in addition to those described above for the GST-immobilized complexes, include immunodetection of complexes using antibodies reactive with the Ras-like protein target molecule, or which are reactive with Ras-like protein and compete with the target molecule, as well as enzyme-linked assays which rely on detecting an enzymatic activity associated with the target molecule.

Agents that modulate one of the Ras-like proteins of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of Ras-like protein activity identified according to these drug screening assays can be used to treat a subject with a disorder mediated by the Ras-like protein associated pathway, by treating cells that express the Ras-like protein. Experimental data as provided in FIG. 1 indicates expression in humans in placenta choriocarcinomas, uterus endometrium adenocarcinomas, skin melanotic melanomas, and fetal brain. These methods of treatment include the steps of administering the modulators of protein activity in a pharmaceutical composition as described herein, to a subject in need of such treatment.

In yet another aspect of the invention, the Ras-like proteins can be used as "bait proteins" in a two-hybrid assay or three-hybrid assay (see, e.g., U.S. Pat. No. 5,283,317; Zervos et al., Cell 72:223–232 (1993); Madura et al., J. Biol. Chem. 268:12046–12054 (1993); Bartel et al., Biotechniques 14:920–924 (1993); Iwabuchi et al., Oncogene 8:1693–1696 (1993); and Brent WO94/10300), to identify other proteins that bind to or interact with the Ras-like protein and are involved in Ras-like protein activity. Such Ras-like protein-binding proteins are also likely to be involved in the propagation of signals by the Ras-like proteins or Ras-like protein targets as, for example, downstream elements of a Ras-like protein-mediated signaling pathway, e.g., a pain signaling pathway. Alternatively, such Ras-like protein-binding proteins are likely to be Ras-like protein inhibitors.

The two-hybrid system is based on the modular nature of most transcription factors, which consist of separable DNA-binding and activation domains. Briefly, the assay utilizes two different DNA constructs. In one construct, the gene that codes for a Ras-like protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Ras-like protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Ras-like protein.

This invention further pertains to novel agents identified by the above-described screening assays. Accordingly, it is within the scope of this invention to further use an agent identified as described herein in an appropriate animal model. For example, an agent identified as described herein (e.g., a Ras-like protein modulating agent, an antisense Ras-like protein nucleic acid molecule, a Ras-like protein-specific antibody, or a Ras-like protein-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The Ras-like proteins of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. Experimental data as provided in FIG. 1 indicates expression in humans in placenta choriocarcinomas, uterus endometrium adenocarcinomas, skin melanotic melanomas, and fetal brain. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in placenta choriocarcinomas, uterus endometrium adenocarcinomas, skin melanotic melanomas, and fetal brain. Accordingly, methods for treatment include the use of the Ras-like protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The fill-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the Ras-like proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the Ras-like proteins of the present invention are expressed in humans in placenta choriocarcinomas, uterus endometrium adenocarcinomas, and skin melanotic melanomas, as indicated by virtual northern blot analysis. In addition, PCR-based tissue screening panels indicate expression in fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in placenta choriocarcinomas, uterus endometrium adenocarcinomas, skin melanotic melanomas, and fetal brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in placenta choriocarcinomas, uterus endometrium adenocarcinomas, skin melanotic melanomas, and fetal brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in placenta choriocarcinomas, uterus endometrium adenocarcinomas, skin melanotic melanomas, and fetal brain. Thus, where a specific protein has been correlated with expression in a specific tissue, antibodies that are specific for this protein can be used to identify a tissue type.

The antibodies are also useful for inhibiting protein function, for example, blocking the binding of the Ras-like protein to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a Ras-like protein polypeptide of the present invention. Such nucleic acid molecules will consist of, consist essentially of, or comprise a nucleotide sequence that encodes one of the Ras-like protein polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3,genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the Ras-like protein polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the Ras-like proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. The gene encoding the novel Ras-like protein of the present invention is located on a genome component that has been mapped to human chromosome 22 (as indicated in FIG. 3), which is supported by multiple lines of evidence, such as STS and BAC map data.

FIG. 3 provides information on SNPs that have been found in the gene encoding the Ras-like protein of the present invention. The following variations were identified: C3951T, C4127T, G4157A, C4513T, C6894A, G8409C, T8437G, T8579C, A10292G, and A10792G. These SNPs may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C., followed by one or more washes in 0.2×SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, the following SNPs have been identified: C3951T, C4127T, G4157A, C4513T, C6894A, G8409C, T8437G, T8579C, A10292G, and A10792G.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel Ras-like protein of the present invention is located on a genome component that has been mapped to human chromosome 22 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that the Ras-like proteins of the present invention are expressed in humans in placenta choriocarcinomas, uterus endometrium adenocarcinomas, and skin melanotic melanomas, as indicated by virtual northern blot analysis. In addition, PCR-based tissue screening panels indicate expression in fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Ras-like protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a Ras-like protein, such as by measuring a level of a receptor-encoding nucleic acid in a sample of cells from a subject e.g., mRNA or genomic DNA, or determining if a receptor gene has been mutated. Experimental data as provided in FIG. 1 indicates that the Ras-like proteins of the present invention are expressed in humans in placenta choriocarcinomas, uterus endometrium adenocarcinomas, and skin melanotic melanomas, as indicated by virtual northern blot analysis. In addition, PCR-based tissue screening panels indicate expression in fetal brain.

Nucleic acid expression assays are useful for drug screening to identify compounds that modulate Ras-like protein nucleic acid expression.

The invention thus provides a method for identifying a compound that can be used to treat a disorder associated with nucleic acid expression of the Ras-like protein gene, particularly biological and pathological processes that are mediated by the Ras-like protein in cells and tissues that express it. Experimental data as provided in FIG. 1 indicates expression in humans in placenta choriocarcinomas, uterus endometrium adenocarcinomas, skin melanotic melanomas, and fetal brain. The method typically includes assaying the ability of the compound to modulate the expression of the Ras-like protein nucleic acid and thus identifying a compound that can be used to treat a disorder characterized by undesired Ras-like protein nucleic acid expression. The assays can be performed in cell-based and cell-free systems. Cell-based assays include cells naturally expressing the Ras-like protein nucleic acid or recombinant cells genetically engineered to express specific nucleic acid sequences.

The assay for Ras-like protein nucleic acid expression can involve direct assay of nucleic acid levels, such as mRNA levels, or on collateral compounds involved in the signal pathway. Further, the expression of genes that are up- or down-regulated in response to the Ras-like protein signal pathway can also be assayed. In this embodiment the regulatory regions of these genes can be operably linked to a reporter gene such as luciferase.

Thus, modulators of Ras-like protein gene expression can be identified in a method wherein a cell is contacted with a candidate compound and the expression of mRNA determined. The level of expression of Ras-like protein mRNA in the presence of the candidate compound is compared to the level of expression of Ras-like protein mRNA in the absence of the candidate compound. The candidate compound can then be identified as a modulator of nucleic acid expression based on this comparison and be used, for example to treat a disorder characterized by aberrant nucleic acid expression. When expression of MRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate Ras-like protein nucleic acid expression in cells and tissues that express the Ras-like protein. Experimental data as provided in FIG. 1 indicates that the Ras-like proteins of the present invention are expressed in humans in placenta choriocarcinomas, uterus endometrium adenocarcinomas, and skin melanotic melanomas, as indicated by virtual northern blot analysis. In addition, PCR-based tissue screening panels indicate expression in fetal brain. Modulation includes both up-regulation (i.e. activation or agonization) or down-regulation (suppression or antagonization) of nucleic acid expression.

Alternatively, a modulator for Ras-like protein nucleic acid expression can be a small molecule or drug identified using the screening assays described herein as long as the drug or small molecule inhibits the Ras-like protein nucleic acid expression in the cells and tissues that express the protein. Experimental data as provided in FIG. 1 indicates expression in humans in placenta choriocarcinomas, uterus endometrium adenocarcinomas, skin melanotic melanomas, and fetal brain.

The nucleic acid molecules are also useful for monitoring the effectiveness of modulating compounds on the expression or activity of the Ras-like protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in Ras-like protein nucleic acid, and particularly in qualitative changes that lead to pathology. The nucleic acid molecules can be used to detect mutations in Ras-like protein genes and gene expression products such as mRNA. The nucleic acid molecules can be used as hybridization probes to detect naturally occurring genetic mutations in the Ras-like protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the Ras-like protein gene associated with a dysfunction provides a diagnostic tool for an active disease or susceptibility to disease when the disease results from overexpression, underexpression, or altered expression of a Ras-like protein.

Individuals carrying mutations in the Ras-like protein gene can be detected at the nucleic acid level by a variety of techniques. FIG. 3 provides information on SNPs that have been found in the gene encoding the Ras-like protein of the present invention. The following variations were identified: C3951T, C4127T, G4157A, C4513T, C6894A, G8409C, T8437G, T8579C, A10292G, and A10792G. These SNPs may affect control/regulatory elements. The gene encoding the novel Ras-like protein of the present invention is located on a genome component that has been mapped to human chromosome 22 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a Ras-like protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant Ras-like protein gene and a wild-type gene can be determined by direct DNA sequencing. A variety of automated sequencing procedures can be utilized when performing the diagnostic assays (Naeve, C. W., *Biotechniques* 19:448 (1995)), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 21 7:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the Ras-like protein gene in an individual in order to select an appropriate compound or dosage regimen for treatment. FIG. 3 provides information on SNPs that have been found in the gene encoding the Ras-like protein of the present invention. The following variations were identified: C3951T, C4127T, G4157A, C4513T, C6894A, G8409C, T8437G, T8579C, A10292G, and A10792G. These SNPs may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control Ras-like protein gene expression in cells, tissues, and organisms. A DNA antisense nucleic acid molecule is designed to be complementary to a region of the gene involved in transcription, preventing transcription and hence production of Ras-like protein. An antisense RNA or DNA nucleic acid molecule would hybridize to the mRNA and thus block translation of mRNA into Ras-like protein.

Alternatively, a class of antisense molecules can be used to inactivate mRNA in order to decrease expression of Ras-like protein nucleic acid. Accordingly, these molecules can treat a disorder characterized by abnormal or undesired Ras-like protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the Ras-like protein, such as ligand binding.

The nucleic acid molecules also provide vectors for gene therapy in patients containing cells that are aberrant in Ras-like protein gene expression. Thus, recombinant cells, which include the patient's cells that have been engineered ex vivo and returned to the patient, are introduced into an individual where the cells produce the desired Ras-like protein to treat the individual.

The invention also encompasses kits for detecting the presence of a Ras-like protein nucleic acid in a biological sample. Experimental data as provided in FIG. 1 indicates that the Ras-like proteins of the present invention are expressed in humans in placenta choriocarcinomas, uterus endometrium adenocarcinomas, and skin melanotic melanomas, as indicated by virtual northern blot analysis. In addition, PCR-based tissue screening panels indicate expression in fetal brain. For example, the kit can comprise reagents such as a labeled or labelable nucleic acid or agent capable of detecting Ras-like protein nucleic acid in a biological sample; means for determining the amount of Ras-like protein nucleic acid in the sample; and means for comparing the amount of Ras-like protein nucleic acid in the sample with a standard. The compound or agent can be packaged in a suitable container. The kit can further comprise instructions for using the kit to detect Ras-like protein mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/ peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the Ras-like protein of the present invention. The following variations were identified: C3951T, C4127T, G4157A, C4513T, C6894A, G8409C, T8437G, T8579C, A10292G, and A10792G. These SNPs may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified Ras-like protein genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, he adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroRas-like protein. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a Ras-like protein polypeptide that can be further purified to produce desired amounts of Ras-like protein or fragments. Thus, host cells containing expression vectors are useful for peptide production.

Host cells are also useful for conducting cell-based assays involving the Ras-like protein or Ras-like protein fragments. Thus, a recombinant host cell expressing a native Ras-like protein is useful for assaying compounds that stimulate or inhibit Ras-like protein function.

Host cells are also useful for identifying Ras-like protein mutants in which these functions are affected. If the mutants naturally occur and give rise to a pathology, host cells containing the mutations are useful to assay compounds that have a desired effect on the mutant Ras-like protein (for example, stimulating or inhibiting function) which may not be indicated by their effect on the native Ras-like protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a Ras-like protein and identifying and evaluating modulators of Ras-like protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the Ras-like protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the Ras-like protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, Ras-like protein activation, and signal transduction, may not be evident from in vitro cell-free or cell-based assays. Accordingly, it is useful to provide non-human transgenic animals to assay in vivo Ras-like protein function, including ligand interaction, the effect of specific mutant Ras-like proteins on Ras-like protein function and ligand interaction, and the effect of chimeric Ras-like proteins. It is also possible to assess the effect of null mutations, which is mutations that substantially or completely eliminate one or more Ras-like protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated nucleic acid molecule consisting of a nucleotide sequence selected from the group consisting of:
   (a) a nucleotide sequence that encodes a protein comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. An isolated polynucleotide consisting of a nucleotide sequence set forth in SEQ ID NO:1.

3. An isolated polynucleotide consisting of a nucleotide sequence set forth in SEQ ID NO:3.

4. A nucleic acid vector comprising a nucleic acid molecule of claim 1.

5. A vector according to claim 4, wherein said vector is selected from the group consisting of a plasmid, virus, and bacteriophage.

6. A vector according to claim 4, wherein said isolated nucleic acid molecule is inserted into said vector in proper orientation and correct reading frame such that the protein of SEQ ID NO:2 may be expressed by a cell transformed with said vector.

7. A vector according to claim 6, wherein said isolated nucleic acid molecule is operatively linked to a promoter sequence.

8. An isolated host cell containing the vector of claim 4.

9. A process for producing a polypeptide comprising culturing the host cell of claim 8 under conditions sufficient for the production of said polypeptide, and recovering said polypeptide from the host cell culture.

10. A method for detecting the presence of a nucleic acid molecule of claim 1 in a sample, said method comprising
    contacting the sample with an oigonucleotide comprising at least 20 contiguous nucleotides that hybridizes to said nucleic acid molecule under stringent conditions, wherein the stringent condition is hybridization in 6× sodium chloride/sodium citrate (SSC) at about 45° C., followed by one or more washes in 0.2×SCC, 0.1% SDS at 50–65° C., and
    determining whether the oligonucleotide binds to said nucleic acid molecule in the sample.

* * * * *